United States Patent
Liu et al.

(10) Patent No.: US 11,547,741 B2
(45) Date of Patent: Jan. 10, 2023

(54) METHODS OF USE OF SOLUBLE CD24 FOR TREATING IMMUNE RELATED ADVERSE EVENTS IN CANCER THERAPIES

(71) Applicants: ONCOIMMUNE, INC., Rockville, MD (US); CHILDREN'S NATIONAL MEDICAL CENTER, Washington, DC (US)

(72) Inventors: Yang Liu, Washington, DC (US); Pan Zheng, Washington, DC (US); Martin Devenport, Gaithersburg, MD (US); Mingyue Liu, Baltimore, MD (US)

(73) Assignees: OncoImmune, Inc., Wilmington, DE (US); Children's National Medical Center, Washington, DC (US)

( * ) Notice: Subject to any disclaimer, the term of this patent is extended or adjusted under 35 U.S.C. 154(b) by 0 days.

(21) Appl. No.: 16/614,660

(22) PCT Filed: May 21, 2018

(86) PCT No.: PCT/US2018/033728
§ 371 (c)(1),
(2) Date: Nov. 18, 2019

(87) PCT Pub. No.: WO2018/217659
PCT Pub. Date: Nov. 29, 2018

(65) Prior Publication Data
US 2020/0197485 A1    Jun. 25, 2020

Related U.S. Application Data

(60) Provisional application No. 62/509,498, filed on May 22, 2017.

(51) Int. Cl.
*A61K 38/17* (2006.01)
*A61P 37/06* (2006.01)
*C07K 14/705* (2006.01)

(52) U.S. Cl.
CPC ............ *A61K 38/177* (2013.01); *A61P 37/06* (2018.01); *C07K 14/70596* (2013.01);
(Continued)

(58) Field of Classification Search
None
See application file for complete search history.

(56) References Cited

U.S. PATENT DOCUMENTS

| 5,541,087 A * | 7/1996 | Lo | C07K 14/005 435/252.3 |
|---|---|---|---|
| 2003/0106084 A1* | 6/2003 | Liu | A61P 37/06 800/18 |
| 2013/0136739 A1* | 5/2013 | Zheng | C07K 14/70596 424/134.1 |

FOREIGN PATENT DOCUMENTS

WO    WO-2016073704 A1 *    5/2016    ............. C07K 14/54

OTHER PUBLICATIONS

Toubai et al. "Donor T Cells Intrinsic Responses to DAMPs Regulated by Siglec-G-CD24 Axis Mitigate GVHD but Maintain GVL in Experimental Allogeneic Stem Cell Transplantation"; Biology of Blood and Marrow Transplantation vol. 22, Issue 3, Supplement, Mar. 2016, pp. S57-S58. (Year: 2016).*

(Continued)

*Primary Examiner* — Joanne Hama
*Assistant Examiner* — Miles Joseph Delahoussaye
(74) *Attorney, Agent, or Firm* — Stanek Lemon Crouse & Meeks, PA

(57) ABSTRACT

The present invention relates to a CD24 protein for treating immune-related adverse events (irAEs) associated with cancer immunotherapy. Provided herein is a method of treating, mitigating, minimizing, or preventing immunerelated adverse events (irAEs) associated with a cancer immunotherapy by administering a CD24 protein to a subject in need thereof. The irAE may be diarrhea or another gastrointesti- (Continued)

```
MGRAMVARLGLGLLLLALLLPTQIYSSETTTGTSSNSSQSTSNSGLAP
NPTNATTKPKSCDKTHTCPPCPAPELLGGPSVFLFPPKPKDTLMISRT
PEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLP
PSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

MGRAMVARLGLGLLLLALLLPTQIYSSETTTGTSSNSSQSTSNSGLAP
NPTNATTKVPKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK
``` nal disorder, pure red cell aplasia, microcytic anemia, lupus, autoimmune nephritism, autoimmune hepatitis, pneumonitis, myocarditis, pericarditis, endocrinopathy, Addison's disease, hypogonadism, Sjogren's syndrome, or type I diabetes. The CCD24 protein may comprise a mature human CD24 or a variant thereof.

16 Claims, 15 Drawing Sheets

Specification includes a Sequence Listing.

(52) U.S. Cl.
CPC ...... C07K 2317/21 (2013.01); C07K 2317/41 (2013.01); C07K 2317/524 (2013.01); C07K 2317/526 (2013.01); C07K 2317/528 (2013.01); C07K 2317/53 (2013.01); C07K 2317/94 (2013.01); C07K 2319/30 (2013.01)

(56) References Cited

OTHER PUBLICATIONS

Negrin et al. "Graft-versus-host disease versus graft-versus-leukemia" Hematology Am Soc Hematol Educ Program (2015) 2015 (1): 225-230. (Year: 2015).*
Scarpati et al. "Ipilimumab in the treatment of metastatic melanoma: management of adverse events"; OncoTargets and Therapy 2014:7 203-209. (Year: 2014).*
Wolchok et al. "Nivolumab plus Ipilimumab in Advanced Melanoma"; N Engl J Med 2013; 369:122-133. (Year: 2013).*
Hughes et al. "Precipitation of Autoimmune Diabetes With Anti-PD-1 Immunotherapy"; Diabetes Care 2015;38:e55-e57. (Year: 2015).*
Schmitt et al. "New Strategies in Engineering T-cell Receptor Gene-Modified T cells to More Effectively Target Malignancies"; Clin. Cancer Res. 21(23) Dec. 1, 2015. (Year: 2015).*
Bleckman et al. "O-glycosylation pattern of CD24 from mouse brain"; Biol. Chem., vol. 390, pp. 627-645, Jul. 2009. (Year: 2009).*
Durocher and Butler. "Expression systems for therapeutic glycoprotein production"; Current Opinion in Biotechnology 2009, 20:700-707. (Year: 2009).*
Saito et al. "Post-liberation cleavage of signal peptides is catalyzed by the site-2 protease (S2P) in bacteria"; PNAS Aug. 16, 2011 108 (33) 13740-13745. (Year: 2011).*
Baskar et al. Cancer and radiation therapy: current advances and future directions. Int J Med Sci. 2012;9(3):193-9 (Year: 2012).*
Kang et al. HMGB1 in cancer: good, bad, or both? Clin Cancer Res. Aug. 1, 2013;19(15):4046-57 (Year: 2013).*
Bleckman et al in "O-glycosylation pattern of CD24 from mouse brain"; Biol. Chem., vol. 390, pp. 627-645, Jul. 2009 (Year: 2009).*
Li et al. Toll-like receptor 4 on islet β cells senses expression changes in high-mobility group box 1 and contributes to the initiation of type 1 diabetes. Exp Mol Med. Apr. 30, 2012;44(4):260-7 (Year: 2012).*
Saito et al. "Post-liberation cleavage of signal peptides is catalyzed by the site-2 protease (S2P) in bacteria"; PNAS Aug. 16, 2011 108 (33) 13740-45 (Year: 2011).*
Durocher and Butler in "Expression systems for therapeutic glycoprotein production"; Current Opinion in Biotechnology 2009, 20: 700-707 (Year: 2009).*
Chen et al. CD24 and Siglec-10 selectively repress tissue damage-induced immune responses. Science. Mar. 27, 2009;323(5922): 1722-5 (Year: 2009).*
Dong et al. High Mobility Group Box I (HMGB1) Release from Tumor Cells After Treatment; Implications for Development of Targeted Chemoimmunotherapy. J Immunother 2007: 30:596-606 (Year: 2007).*
Sattler, Susanne, and Teresa Kennedy-Lydon, eds. The Immunology of Cardiovascular Homeostasis and Pathology. vol. 10. Springer International Publishing, 2017 (Year: 2017).*
Boyapati et al. Gut mucosal DAMPS in IBD: from mechanisms to therapeutic implications. Mucosal Immunology 2016 9(3): 567-582 (Year: 2016).*
Hoos A. Development of immuno-oncology drugs—from CTLA4 to PD1 to the next generations. Nat Rev Drug Discov. Apr. 2016;15(4):235-47 (Year: 2016).*
Weber et al. Management of Immune-Related Adverse Events and Kinetics of Response with Ipilimumab. Journal of Clinical Oncology 2012 30(21): 2691-2697 (Year: 2012).*
Czajkowsky et al. "Fc-fusion proteins: new developments and future perspectives"; EMBO Mol Med (2012) 4, 1015-1028 (Year: 2012).*

* cited by examiner

FIG. 1A

<u>MGRAMVARLGLGLLLLALLLPTQIYS</u>SETTTGTSSNSSQSTSNSGLAP
NPTNATTKPKSCDKTHTCPPCPAPELLGGPSVFLFPPKPKDTLMISRT
PEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLP
PSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

FIG. 1B

<u>MGRAMVARLGLGLLLLALLLPTQIYS</u>SETTTGTSSNSSQSTSNSGLAP
NPTNATTK<u>V</u>PKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 1C

<u>MGRAMVARLGLGLLLLALLLPTQIYS</u>SETTTGTSSNSSQSTSNSGLAP
NPTNATTK<u>A</u>PKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 2

```
Mouse CD24 NQTSVAPFPGN--QNISAS----PNPTNATTRG
           _*   _     *  *   * *     ********__
Human CD24 SETTTGTSS-NSSQSTSNS-GLAPNPTNATTKA(V)
```

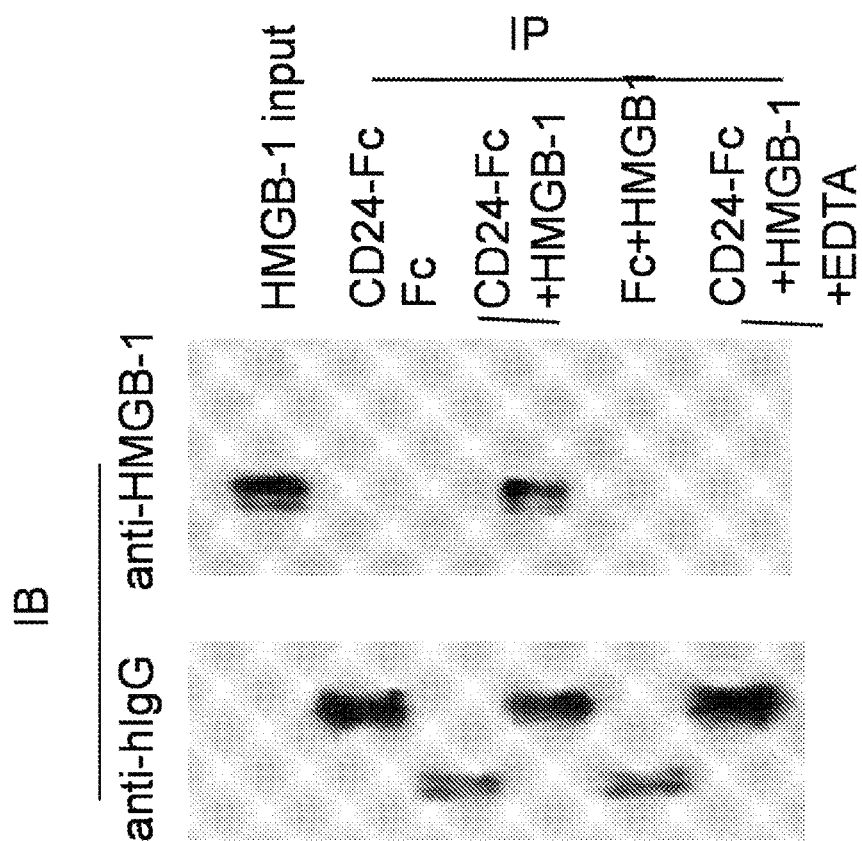

METHODS OF USE OF SOLUBLE CD24 FOR TREATING IMMUNE RELATED ADVERSE EVENTS IN CANCER THERAPIES

FIELD OF THE INVENTION

The present invention relates to the use of a CD24 protein for treating immune-related adverse events (irAEs) associated with cancer immunotherapy.

BACKGROUND OF THE INVENTION

The immune system has the ability to recognize and eliminate cancers in experimental model systems and in patients. As a result, cancer immunotherapies are emerging as one of the most promising areas of cancer therapy. Active cancer immunotherapies involve agents that amplify natural immune responses (including antibodies against PD-1, PD-L1 or CTLA-4); small molecules that modulate tumor microenvironment; or, adoptive cell transfer (ACT) using ex vivo stimulated tumor infiltrating lymphocytes (TILs), activated natural killer (NK) cells, or genetically-engineered T cells (chimeric antigen receptors [CARS] and T cell receptor [TCR] modified T cells). Alternatively, other cancer immunotherapies that target the tumor directly can indirectly cause activation of the immune system (including cancer-targeting antibodies such as anti-Her-2 antibodies in cases of solid cancer, anti-CD20 antibodies in cases of B-cell malignancies, or anti-GM2 antibodies in cases of neuroblastoma). Antibodies against PD-1, PD-L1 and CTLA-4, as well as tumor targeting antibodies, have demonstrated substantial benefits for treating solid tumors and hematologic tumors. Adoptive cellular immunotherapies such as CAR T cells have demonstrated impressive effects against hematologic tumors such as leukemia, but only limited effects against solid tumors to date. Whereas CAR-T immunotherapies have been targeted more towards hematologic malignancies, T cell immunotherapies using gene-modified TCRs have been targeted more towards solid tumors.

Tumors evade immune elimination by generating highly tolerogenic and immunosuppressive tumor microenvironments (TMEs). Therefore, an important goal of immunooncology is to understand the varied tolerance mechanisms employed by tumors in order to eliminate these mechanisms to allow tumor infiltration, activation, and destruction of tumor cells by the immune system. However, despite their therapeutic promise, systemic delivery of immunotherapies can also lead to breaches in self-tolerance. This in turn results in mild to severe inflammatory reactions across a variety of organ systems, and in some instances, life-threatening autoimmunity, generally referred to as immune-related adverse events (irAEs). As immunotherapy approaches are expanded to more cancer indications and in ever-more-effective combinations, controlling non-specific irAEs will be a critical goal for these next-generation cancer immunotherapies.

Treatment with antibodies against PD-1, PD-L1 and CTLA-4 has been shown to be a powerful tool for enhancing anti-tumor immunity in preclinical models. Monotherapy with an antibody against CTLA4 promoted rejection of transplantable tumors of various origins. Based on promising preclinical tumor model studies, the clinical potential of antibodies against CTLA4 has been explored in different human malignancies. Although anti-CTLA4 (Ipilimumab, marketed as Yervoy, disclosed in U.S. Pat. No. 6,984,720) has demonstrated efficacy in treating melanoma, treatment and targeting of CTLA4 is associated with autoimmune-like toxicities. Anti-PD-1 and anti-PD-L1 antibodies show significantly higher clinical response and significantly lower irAE. However, severe autoimmune adverse events still occur in approximately 15-20% of cancer patients. In addition, anti-CTLA4 mAbs such as Ipilimumab and Tremelimumab are used in combination therapy with anti-PD-1/PD-L1 antibodies with superior therapeutic effect. But the improved therapeutic effect is associated even higher rates of grade 3 and grade 4 organ toxicity. Instances of irAEs have been reported across multiple body sites, including gastrointestinal tract, skin, kidney, pancreas, liver, and central and peripheral nervous systems. The incidence and severity of irAEs correlates with overall patient response and survival to checkpoint blockade, suggesting that both anti-tumor and autoimmune responses are sensitive to anti-checkpoint immunotherapy. Such irAEs may be broadly categorized as "autoimmune toxicity," or so-called "on target, off-tumor toxicity," which results from antigen-specific attack on host tissues when the targeted tumor associated antigen is expressed on nonmalignant tissue. Autoimmune toxicity has resulted in fatal toxicities after infusion of genetically engineered T cells targeting MAGE-A3.

Genetically-engineered T cell therapies, such as CAR-T, are also associated with irAEs that limit their use, although here the adverse events are more commonly cytokine-associated toxicities. CAR-T cells lead to T-cell expansion in vivo, which can lead to the release of toxic levels of cytokines, a systemic inflammatory response referred to variously as cytokine storm or cytokine release syndrome (CRS). Infusion reactions are also common with antibody and Fc-fusion protein therapeutics, and are associated with symptoms ranging from mild nausea and fever, to life threatening multiple organ failure. Aggressive supportive care is necessary for all patients experiencing CAR T-cell toxicities, with early intervention for hypotension and treatment of concurrent infections being essential. However, pharmacologic management is complicated by the risk of immunosuppressive therapy abrogating the anti-malignancy activity of the CAR T cells and is the major reason why prophylactic immunosuppression is not used. Interleukin-6 receptor blockade with tocilizumab remains the mainstay pharmacologic therapy for CRS, though indications for administration vary among treating centers.

CRS has also occurred with other forms of cancer therapy associated with rapid lysis of malignant cells, resulting in acute anaphylaxis or a phenomenon called tumor lysis syndrome (TLS). Since cell lysis can cause the release of intracellular components called danger (damage)-associated molecular patterns (DAMPs), it can cause inflammation and set the stages for autoimmune disease if not properly controlled. However, traditional immune suppressants may be problematic for adverse events in cancer therapy as all forms of cancer therapies are believed to require anti-cancer immune responses either directly or indirectly.

Accordingly, there is a large unmet medical need for treating irAEs while preserving cancer immunity.

SUMMARY OF THE INVENTION

Provided herein is a method of treating, mitigating, minimizing, or preventing immune-related adverse events (irAEs) associated with a cancer immunotherapy by administering a CD24 protein to a subject in need thereof. The irAE may be diarrhea or another gastrointestinal disorder, pure red cell aplasia, microcytic anemia, lupus, autoimmune nephritis, autoimmune hepatitis, pneumonitis, myocarditis, pericarditis, endocrinopathy, Addison's disease, hypogonadism, Sjogren's syndrome, or type I diabetes. The CD24 protein may comprise a mature human CD24 or a variant thereof. The sequence of the mature human CD24 may comprise an amino acid sequence set forth in SEQ ID NO: 1 or 2. The CD24 protein may comprise any or all of the extracellular domain of human CD24. The sequence of the CD24 protein may comprise the signal sequence having an amino acid sequence set forth in SEQ ID NO: 4 to allow secretion from a cell expressing the protein. The signal peptide sequence may be one that is found on other transmembrane or secreted proteins, or one modified from the existing signal peptides known in the art. The CD24 protein may be soluble and/or may be glycosylated. The CD24 protein may be produced using an eukaryotic protein expression system, which may comprise a vector contained in a Chinese Hamster Ovary cell line or a replication-defective retroviral vector. The replication defective retroviral vector may be stably integrated into the genome of a eukaryotic cell.

The CD24 protein may comprise a protein tag, which may be fused at the N- or C-terminus of the CD24 protein. The protein may comprise a portion of a mammalian immunoglobulin (Ig), which may be the Fc region of a human Ig protein. The human Ig protein may comprise the hinge region and CH2 and CH3 domains of the human Ig protein, and the human Ig protein may be IgG1, IgG2, IgG3, IgG4, or IgA. The Fc region may also comprise the hinge region and CH2, CH3, and CH4 domains of IgM. The CD24 protein may comprise an amino acid sequence set forth in SEQ ID NO: 5, 6, 8, 9, 11, or 12.

The cancer immunotherapy may be an anti-CTLA4 antibody, which may be Ipilimumab. The anti-CTLA4 antibody may be administered in combination with another therapy. The cancer therapy may also be an anti-PD-1 antibody, which may be administered in combination with another therapy. The cancer therapy may also be an anti-PD-L1 antibody, which may be administered in combination with another therapy. The cancer therapy may also be a chimeric antigen T cell, a T cell receptor modified T cell, or an activated natural killer cell. The cancer therapy may also be irradiation therapy, chemotherapy, or a cancer therapy that involves a cancer cell-targeting antibody.

Also described herein is a method of treating, reducing, or preventing graft versus host disease (GvHD) in a subject that may receive, have received or be receiving activated Natural Killer (aNK) cells following allogeneic hematopoietic stem cell transplantation (HSCT) by administering the CD24 protein to a subject in need thereof.

Further described herein is a method of prophylaxis or treatment of irAEs associated with massive tumor lysis during a cancer therapy by administering the CD24 to a subject in need thereof. The cancer therapy may be a radiation therapy, chemotherapy, or an anti-cancer antibody that causes direct killing of cancer cells.

BRIEF DESCRIPTION OF THE DRAWINGS

FIG. 1A shows the amino acid composition of the full length CD24 fusion protein, CD24Fc (also referred to herein as CD24Ig) (SEQ ID NO: 5). The underlined 26 amino acids are the signal peptide of CD24 (SEQ ID NO: 4), which are cleaved off during secretion from a cell expressing the protein and thus missing from the processed version of the protein (SEQ ID NO: 6). The bold portion of the sequence is the extracellular domain of the mature CD24 protein used in the fusion protein (SEQ ID NO: 2). The last amino acid (A or V) that is ordinarily present in the mature CD24 protein has been deleted from the construct to avoid immunogenicity. The non-underlined, non-bold letters are the sequence of IgG1 Fc, including the hinge region and CH1 and CH2 domains (SEQ ID NO: 7). FIG. 1B shows the sequence of CD24$^V$Fc (SEQ ID NO: 8), in which the mature human CD24 protein (bold) is the valine polymorphic variant of SEQ ID NO: 1. FIG. 1C shows the sequence of CD24$^4$Fc (SEQ ID NO: 9), in which the mature human CD24 protein (bold) is the alanine polymorphic variant of SEQ ID NO: 1. The various parts of the fusion protein in FIGS. 1B and 1C are marked as in FIG. 1A and the variant valine/alanine amino acid is double underlined.

FIG. 2 shows amino acid sequence variations between mature CD24 proteins from mouse (SEQ ID NO: 3) and human (SEQ ID NO: 2). The potential O-glycosylation sites are bolded, and the N-glycosylation sites are underlined.

FIG. 3A. i.v. injection of 1 mg CD24IgG1. FIG. 3B. s.c. injection of 1 mg CD24IgG1 (CD24Fc). FIG. 3C. Comparison of the total amounts of antibody in the blood as measured by areas under curve (AUC), half-life and maximal blood concentration. Note that overall, the AUC and Cmax of the s.c. injection is about 80% of i.v. injection, although the difference is not statistically significant.

FIG. 4A. Host response to PAMP was unaffected by CD24-Siglec G(10) interaction. FIG. 4B. CD24-Siglec G (10) interaction represses host response to DAMP, possibly through the Siglec G/10-associated SHP-1.

FIG. 5. CD24 Fc binds to Siglec 10 and HMGB1 and activates Siglec G, the mouse homologue of human Siglec 10. FIG. 5B. CD24-Fc specifically interacts with HMGB-1 in a cation-dependent manner. CD24-Fc was incubated with HMGB1 in 0.1 mM of $CaCl_2$ and $MgCl_2$, in the presence or absence of the cation chelator EDTA. CD24Fc is pulled down with protein G-beads, and the amounts of HMGB1, CD24Fc or control Fc is determined by Western blot.

FIG. 7A. ShRNA silencing of CD24 leads to spontaneous production of TNF-α, IL-1β and IL-6. THP1 cells were transduced with lentiviral vectors encoding either scrambled or two independent CD24 shRNA molecules. The transduced cells were differentiated into macrophages by culturing for 4 days with PMA (15 ng/ml). After washing away PMA and non-adherent cells, the cells were cultured for another 24 hours for measurement of inflammatory cytokines, by cytokine beads array. FIG. 7B. As in FIG. 7A, except that the given concentration of CD24Fc or control IgG Fc was added to macrophages in the last 24 hours. Data shown in FIG. 4A are means and S.D. from three independent experiments, while those in FIG. 4B are representative of at least 3 independent experiments.

DETAILED DESCRIPTION

Figure 3:
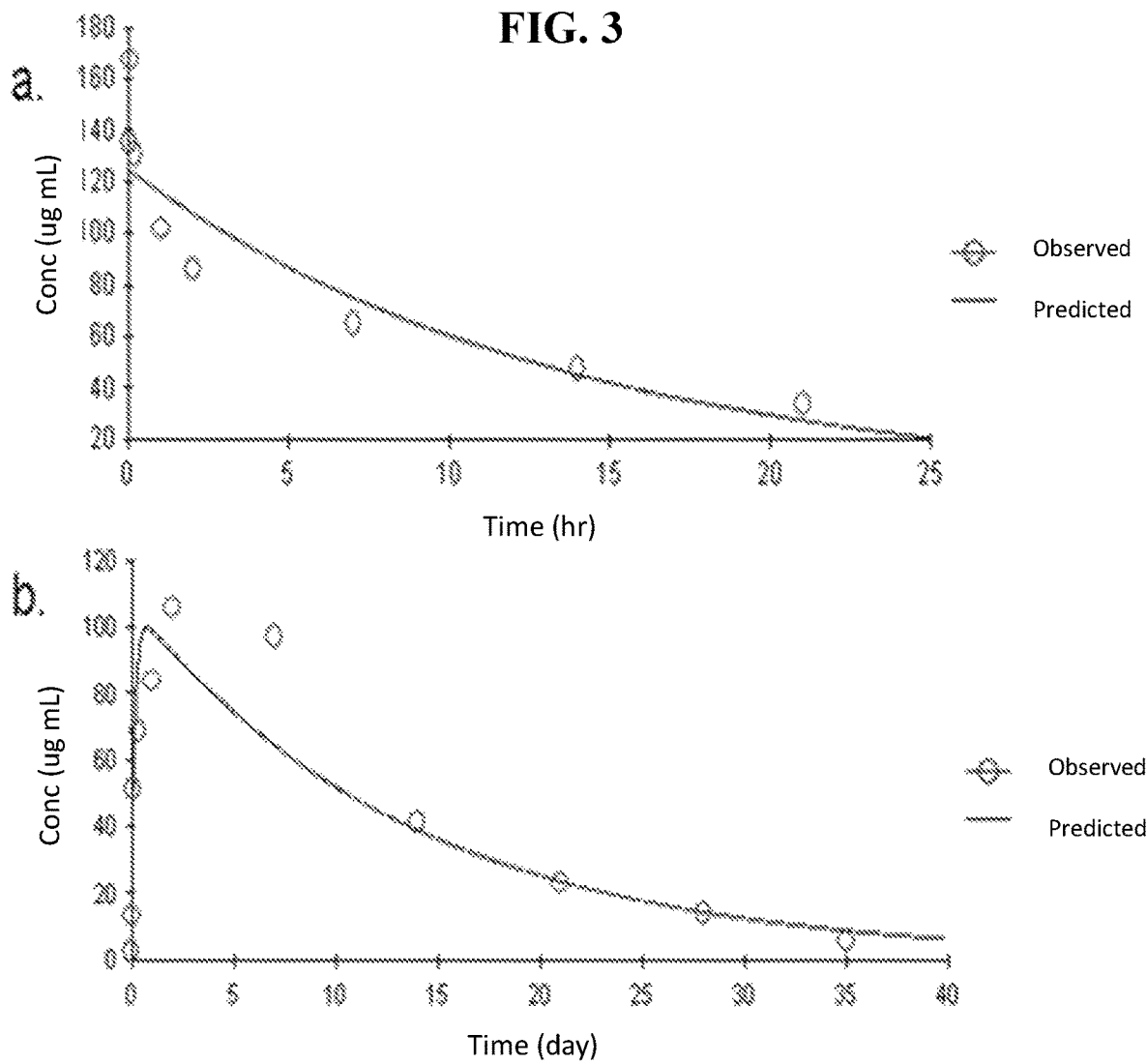
FIG. 3. WinNonlin compartmental modeling analysis of pharmacokenitics of CD24IgG1 (CD24Fc). The opened circles represent the average of 3 mice, and the line is the predicted pharmacokinetic curve.

The inventors have discovered that, surprisingly, a soluble form of CD24 is highly effective for treating immune-related adverse events (irAEs). The effect may be mediated through DAMPs. Pattern recognition is involved in inflammatory response triggered by both pathogen-associated and tissue damage-associated molecular patterns, respectively called PAMPs and DAMPs. The inventors have realized that recent studies have demonstrated that an exacerbated host response to DAMPs may play a part in the pathogenesis of inflammatory and autoimmune disease. DAMPs were found to promote the production of inflammatory cytokines and autoimmune diseases and in animal models, and inhibitors of DAMPs such as HMGB1 and HSP90 were consequently found to ameliorate rheumatoid arthritis (RA) (4-6). TLRs, RAGE-R, DNGR (encoded by Clec9A), and Mincle have been shown to be receptors responsible for mediating inflammation initiated by a variety of DAMPs (2, 7-14).

The inventors' recent work demonstrated that CD24-Siglec G interactions discriminate innate immunity to DAMPs from PAMPs (15, 16). Siglec proteins are membrane-associated immunoglobulin (Ig) superfamily members that recognize a variety of sialic acid-containing structures. Most Siglecs have an intra-cellular immune-tyrosine inhibitory motif (ITIM) that associates with SHP-1, -2 and Cb1-b to control key regulators of inflammatory responses. The inventors have reported CD24 as the first natural ligand for a Siglec, Siglec G in mouse and Siglec 10 in human (15). Siglec G interacts with sialylated CD24 to suppress the TLR-mediated host response to DAMPs, such as HMGB1, via a SHP-1/2 signaling mechanism (15).

Human CD24 is a small GPI-anchored molecule encoded by an open-reading frame of 240 base pairs in the CD24 gene (28). Of the 80 amino acids, the first 26 constitute the signal peptide, while the last 23 serve as a signal for cleavage to allow for the attachment of the GPI tail. As a result, the mature human CD24 molecule has only 31 amino acids. One of the 31 amino acids is polymorphic among the human population. A C to T transition at nucleotide 170 of the open-reading frame results in the substitution of alanine (a) with valine (v). Since this residue is in the immediate N-terminal to the cleavage site, and since the replacement is non-conservative, these two alleles may be expressed at different efficiencies on the cell surface. Indeed, transfection studies with cDNA demonstrated that the $CD24^v$ allele is more efficiently expressed on the cell surface (28). Consistent with this, $CD24^{v/v}$ PBL expressed higher levels of CD24, especially on T cells.

The inventors have demonstrated that CD24 negatively regulates host response to cellular DAMPs that are released as a result of tissue or organ damage, and at least two overlapping mechanisms may explain this activity. First, CD24 binds to several DAMPs, including HSP70, HSP90, HMGB1 and nucleolin and represses host response to these DAMPs. To do this, it is presumed that CD24 may trap the inflammatory stimuli to prevent interaction with their receptors, TLR or RAGE. Second, using an acetaminophen-induced mouse model of liver necrosis and ensuring inflammation, the inventors demonstrated that through interaction with its receptor, Siglec G, CD24 provides a powerful negative regulation for host response to tissue injuries. To achieve this activity, CD24 may bind and stimulate signaling by Siglec G wherein Siglec G-associated SHP1 triggers the negative regulation. Both mechanisms may act in concert as mice with targeted mutation of either gene mounted much stronger inflammatory response. In fact, DC cultured from bone marrow from either CD24–/– or Siglec G–/– mice produced higher levels of inflammatory cytokines when stimulated with either HMGB1, HSP70, or HSP90. To the inventors' knowledge, CD24 is the only inhibitory DAMP receptor capable of shutting down inflammation triggered by DAMPs and no drug is currently available that specifically targets host inflammatory response to tissue injuries. Furthermore, the inventors have demonstrated the ability of exogenous soluble CD24 protein to alleviate DAMP-mediated autoimmune disease using mouse models of RA, MS and GvHD.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

A "peptide" or "polypeptide" is a linked sequence of amino acids and may be natural, synthetic, or a modification or combination of natural and synthetic.

"Substantially identical" may mean that a first and second amino acid sequence are at least 60%, 65%, 70%, 75%, 80%, 85%, 90%, 95%, 96%, 97%, 98%,or 99% over a region of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

A "variant" may mean a peptide or polypeptide that differs in amino acid sequence by the insertion, deletion, or conservative substitution of amino acids, but retain at least one biological activity. Representative examples of "biological activity" include the ability to bind to a toll-like receptor and to be bound by a specific antibody. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge.

It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. CD24

Provided herein is a CD24 protein, which may comprise a mature CD24 or a variant thereof. Mature CD24 corresponds to the extracellular domain (ECD) of CD24. The mature CD24 may be from a human or another mammal. As described above, mature human CD24 protein is 31 amino acids long and has a variable alanine (A) or valine (V) residue at its C-terminal end:

(SEQ ID NO: 1)
SETTTGTSSNSSQSTSNSGLAPNPTNATTK(V/A)

The C-terminal valine or alanine may be immunogenic and may be omitted from the CD24 protein, which may reduce its immunogenicity. Therefore, the CD24 protein may comprise the amino acid sequence of human CD24 lacking the C-terminal amino acid:

(SEQ ID NO: 2)
SETTTGTSSNSSQSTSNSGLAPNPTNATTK

Despite considerable sequence variations in the amino acid sequence of the mature CD24 proteins from mouse and human, they are functionally equivalent, as human CD24Fc has been shown to be active in the mouse. The amino acid sequence of the human CD24 ECD shows some sequence conservation with the mouse protein (39% identity; Genbank accession number NP_033976). However, it is not that surprising that the percent identity is not higher as the CD24 ECD is only 27-31 amino acids in length, depending on the species, and binding to some of its receptor(s), such as Siglec 10/G, is mediated by its sialic acid and/or galactose sugars of the glycoprotein. The amino acid sequence identity between the extracellular domains of the human Siglec-10 (GenBank accession number AF310233) and its murine homolog Siglec-G (GenBank accession number NP_766488) receptor proteins is 63% (FIG. 2). As a result of sequence conservation between mouse and human CD24 primarily in the C-terminus and in the abundance of glycosylation sites, significant variations in the mature CD24 proteins may be tolerated in using the CD24 protein, especially if those variations do not affect the conserved residues in the C-terminus or do not affect the glycosylation sites from either mouse or human CD24. Thus, the CD24 protein may comprise the amino acid sequence of mature murine CD24:

(SEQ ID NO: 3)
NQTSVAPFPGNQNISASPNPTNATTRG.

The amino acid sequence of the human CD24 ECD shows more sequence conservation with the cynomolgus monkey protein (52% identity; UniProt accession number UniProtKB-I7GKK1) than with mouse. Again, this is not surprising given that the percent identity is not higher as the ECD is only 29-31 amino acids in length in these species, and the role of sugar residues in binding to its receptor(s). The amino acid sequence of cynomolgous Siglec-10 receptor has not been determined but the amino acid sequence identity between the human and rhesus monkey Siglec-10 (GenBank accession number XP_001116352) proteins is 89%. Therefore, the CD24 protein may also comprise the amino acid sequence of mature cynomolgous (or rhesus) monkey CD24:

(SEQ ID NO: 10)
TVTTSAPLSSNSPQNTSTTPNPANTTTKA

The CD24 protein may be soluble. The CD24 protein may further comprise an N-terminal signal peptide, to allow secretion from a cell expressing the protein. The signal peptide sequence may comprise the amino acid sequence MGRAMVARLGLGLLLLALLLPTQIYS (SEQ ID NO: 4). Alternatively, the signal sequence may be any of those that are found on other transmembrane or secreted proteins, or those modified from the existing signal peptides known in the art.

a. Fusion

The CD24 protein may be fused at its N- or C-terminal end to a protein tag, which may comprise a portion of a mammalian Ig protein, which may be human or mouse or from another species. The portion may comprise an Fc region of the Ig protein. The Fc region may comprise at least one of the hinge region, CH2, CH3, and CH4 domains of the Ig protein. The Ig protein may be human IgG1, IgG2, IgG3, IgG4, or IgA, and the Fc region may comprise the hinge region, and CH2 and CH3 domains of the Ig. The Fc region may comprise the human immunoglobulin G1 (IgG1) isotype (SEQ ID NO: 7). The Ig protein may also be IgM, and the Fc region may comprise the hinge region and CH2, CH3, and CH4 domains of IgM. The protein tag may be an affinity tag that aids in the purification of the protein, and/or a solubility-enhancing tag that enhances the solubility and recovery of functional proteins. The protein tag may also increase the valency of the CD24 protein. The protein tag may also comprise GST, His, FLAG, Myc, MBP, NusA, thioredoxin (TRX), small ubiquitin-like modifier (SUMO), ubiquitin (Ub), albumin, or a Camelid Ig. Methods for making fusion proteins and purifying fusion proteins are well known in the art.

Based on preclinical research, for the construction of the fusion protein CD24Fc identified in the examples, the truncated form of native CD24 molecule of 30 amino acids, which lacks the final polymorphic amino acid before the GPI signal cleavage site (that is, a mature CD24 protein having SEQ ID NO: 2), has been used. The mature human CD24 sequence is fused to a human IgG1 Fc domain (SEQ ID NO: 7). The full length CD24Fc fusion protein is provided in SEQ ID NO: 5 (FIG. 1), and the processed version of CD24Fc fusion protein that is secreted from the cell (i.e. lacking the signal sequence which is cleaved off) is provided in SEQ ID NO: 6. Processed polymorphic variants of mature CD24 (that is, mature CD24 protein having SEQ ID NO: 1) fused to IgG1 Fc may comprise SEQ ID NO: 11 or 12.

b. Production

The CD24 protein may be heavily glycosylated, and may be involved in functions of CD24 such as costimulation of immune cells and interaction with a damage-associated molecular pattern molecule (DAMP). The CD24 protein may be prepared using a eukaryotic expression system. The expression system may entail expression from a vector in mammalian cells, such as Chinese Hamster Ovary (CHO) cells. The system may also be a viral vector, such as a replication-defective retroviral vector that may be used to infect eukaryotic cells. The CD24 protein may also be produced from a stable cell line that expresses the CD24 protein from a vector or a portion of a vector that has been integrated into the cellular genome. The stable cell line may express the CD24 protein from an integrated replication-defective retroviral vector. The expression system may be GPEx™.

c. Pharmaceutical Composition

The CD24 protein may be contained in a pharmaceutical composition, which may comprise a pharmaceutically acceptable amount of the CD24 protein. The pharmaceutical composition may comprise a pharmaceutically acceptable carrier. The pharmaceutical composition may comprise a solvent, which may keep the CD24 protein stable over an extended period. The solvent may be PBS, which may keep the CD24 protein stable for at least 66 months at −20° C. (−15~−25° C.). The solvent may be capable of accommodating the CD24 protein in combination with another drug.

The pharmaceutical composition may be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

The pharmaceutical composition may also be formulated as a depot preparation, which may be administered by implantation or by intramuscular injection. The composition may be formulated with suitable polymeric or hydrophobic materials (as an emulsion in an acceptable oil, for example), ion exchange resins, or as sparingly soluble derivatives (as a sparingly soluble salt, for example). A formulation for subcutaneous injection may be particularly relevant for an indication like lupus and its associated manifestations and complications.

d. Dosage

The dose of the CD24 protein may ultimately be determined through a clinical trial to determine a dose with acceptable toxicity and clinical efficacy. The initial clinical dose may be estimated through pharmacokinetics and toxicity studies in rodents and non-human primates. The dose of the CD24 protein may be 0.01 mg/kg to 1000 mg/kg, and may be 1 to 500 mg/kg, depending on the desired effect and the route of administration. The CD24 protein may be administered by intravenous infusion or subcutaneous, intramural (that is, within the wall of a cavity or organ), or intraperitoneal injection, and the dose may be 10-1000 mg, 10-500 mg, 10-240 mg, 10-120 mg, or 10, 30, 60, 120, or 240 mg, where the subject is a human.

3. Methods of Treatment a. Immune-Related Adverse Events

Provided herein is a method of mitigating, reducing, minimizing, or treating irAEs by administering the CD24 protein to a subject in need thereof. The irAEs may be associated with a cancer therapy, and the subject may be a cancer patient. The cancer therapy may be a cancer immunotherapy. The CD24 protein may be administered to a subject with or at risk of developing irAEs associated with the cancer therapy. The CD24 protein may be used prophylactically to prevent irAEs before the cancer therapy is initiated or before the clinical signs of irAEs emerge. The CD24 protein may also be administered therapeutically to treat irAEs after the cancer therapy is initiated and the clinical symptoms are diagnosed. The irAE may be diarrhea or another gastrointestinal disorder, pure red cell aplasia, microcytic anemia, lupus, autoimmune nephritis, autoimmune hepatitis, pneumonitis, myocarditis, pericarditis, endocrinopathy, Addison's disease, hypogonadism, Sjogren's syndrome, or type I diabetes.

The cancer therapy may be active immunotherapy. Examples of active immunotherapy include anti-CTLA4, anti-PD-1, anti-PD-L1, anti-TNF, an antibody against another TNF-receptor family member, anti-LAG3, anti-TIM3, and a small or large molecule inhibitor that modulates the tumor microenvironment. In particular, the cancer therapy may be anti-CTLA4 immunotherapy, and the CD24 protein may be administered to a subject in combination with, or on a background of, anti-CTLA4 immunotherapy. Examples of anti-CTLA4 antibodies include Ipilimumab (Yervoy) and Tremilimumab.

In another embodiment, the cancer therapy may be anti-PD-1/PD-L1 immunotherapy, which may be an anti-PD-1 antibody or an anti-PD-L1 antibody. Examples of anti-PD-1 antibodies include nivolumab, (Opdivo-Bristol Myers Squibb) and Pembrolizumab (Keytruda, MK-3475, Merck). Examples of anti-PD-L1 antibodies include Atezolizumab (Tecentriq, Roche), Avelumab (Merck KGaA and Pfizer) and durvalumab (Imfinzi, Astra-Zeneca).

In yet another embodiment, the cancer therapy may be combination therapy comprising anti-CTLA-4 and anti-PD-1 monoclonal antibodies (mAbs). Combination therapy with anti-CTLA-4 and anti-PD-1 has emerged as the most potent and durable cancer immunotherapy. However, the autoimmune adverse effect associated with the combination therapy is quite severe, with greater than 50% of melanoma patients developing grade 3 and 4 organ toxicity. Therefore, a major challenge in cancer immunotherapy is how to reduce adverse effects of the combination therapy without affecting therapeutic efficacy. Of the two components of the combination therapy, anti-CTLA-4 mAb exhibits considerably more immunotherapy-related adverse effects (irAE).

The cancer therapy may be adoptive cell transfer (ACT) using ex vivo stimulated tumor infiltrating lymphocytes (TILs) or genetically-engineered T cells (chimeric antigen receptors [CARS] or T cell receptor [TCR] modified T cells). In particular, by causing rapid death of normal and cancer cells, cancer therapies such as CAR-T cells can cause the release of damage associated molecular patterns (DAMPs) and, consequently, cytokine release syndrome that can also lead to widespread organ dysfunction. Therefore, the CD24 protein may be used to reduce or neutralize the effects of the DAMPs and mitigate, minimize or treat the resulting cytokine storm. CAR-T cell can damage normal cells if they target a tumor-associated antigen that is also expressed on non-tumor cells and tissues. CAR-T therapies may be used in the treatment of hematologic tumors such as acute lymphoblastic leukemia (ALL), B-cell Acute Lymphoblastic Leukemia, adult myeloid leukemia, (AML), diffuse large B-cell lymphoma (DLBCL), non-Hodgkin Lymphoma (NHL), Chronic Lymphocytic Leukemia (CLL), primary mediastinal B-cell lymphoma (PMBCL), mantle cell lymphoma (MCL), and multiple myeloma (MM). Examples of CAR-T therapies include those targeting the B cell surface antigens CD19 (such as JCAR017 and JCAR014 [Juno Therapeutics]), CTL019 (tisagenlecleucel-T [Novartis] and KTE-C19 [axicabtagene ciloleucel, Kite Pharma]), and CD22 (JCAR014 [Juno Therapeutics]). Other examples of CAR-T therapies include those targeting L1-CAM (JCAR023 [Juno Therapeutics]), ROR-1 (JCAR024 [Juno Therapeutics]) and MUC16 (JCAR020 [Juno Therapeutics]). Examples of targets for TCR modified T cells include those targeting MAGE-A3, such as KITE-718 (Kite Pharma), Wilms tumor antigen 1 (WT-1), such as JTCR016 (Juno Therapeutics), and NY-ESO-1.

The cancer therapy may be one that involves rapid killing of cancer cells, such as irradiation and chemotherapy. The resulting tumor lysis can lead to the release of DAMPs that initiate an inflammatory cascade. Such indications may be particularly amenable to prophylactic treatment with the CD24 protein.

b. Graft Versus Host Disease

Also provided herein is a method of reducing or treating graft versus host disease (GvHD) in a subject that may have received or be receiving activated Natural Killer (aNK) cells following allogeneic hematopoietic stem cell transplantation (HSCT) by administering the CD24 protein to a subject in need thereof. NK cells can enhance engraftment and mediate graft-versus-leukemia following allogeneic HSCT, but the potency of graft-versus-leukemia mediated by naturally reconstituting NK cells following HSCT is limited. Preclinical studies demonstrate that activation of NK cells upregulates activating receptor expression and augments killing capacity (Shah et al 2015). This was then tested in a clinical trial studying the adoptive transfer of donor-derived activated NK cells (aNK-DLI) following HLA-matched, T-cell-depleted nonmyeloablative peripheral blood stem cell transplantation in children and young adults with ultra-high-risk solid tumors. aNK-DLI demonstrated potent killing capacity and displayed high levels of activating receptor expression. However, 5 of 9 transplant recipients experienced acute graft-versus-host disease (GVHD) following aNK-DLI, with grade 4 GVHD observed in 3 subjects. GVHD was more common in matched unrelated donor vs matched sibling donor recipients and was associated with higher donor CD3 chimerism. Given that the T-cell dose was below the threshold required for GVHD in this setting, it was concluded that aNK-DLI contributed to the acute GVHD observed, likely by augmenting underlying T-cell alloreactivity.

c. Administration

The route of administration of the pharmaceutical composition may be parenteral. Parenteral administration includes, but is not limited to, intravenous, intraarterial, intraperitoneal, subcutaneous, intramuscular, intrathecal, intraarticular, and direct injection. The pharmaceutical composition may be administered to a human patient, cat, dog, or large animal. The composition may be administered 1, 2, 3, 4, 5, 6, 7, 8, 9, 10, 11, or 12 times per day.

d. Combination Treatment

The CD24 protein may be used in combination with another agent to further reduce, mitigate or treat cytokine release syndrome (CRS). Cytokine release syndrome is associated with elevated circulating levels of several cytokines including interleukin (IL)-6 and IFN-γ. Accordingly, the other agent may be tocilizumab (Actemra), an anti-IL-6 receptor antibody, or another cytokine targeting agent, with or without corticosteroids, which may be used for immunosuppression and may be used to reverse the syndrome, particularly in patients receiving CAR-T. The other agent used for CRS management may be siltuximab (anti-IL-6, Sylvant), etanercept (TNFα inhibitor, Enbrel), infliximab (anti-TNFα, Remicade), or anakinra (interleukin 1 receptor antagonist, Kineret). The CD24 protein may be used to target and mitigate the effect of DAMPs that are released from the damaged tissue and which initiate the inflammatory cascade, while the combination therapy may target the effector cytokine molecule, thereby providing a complementary two-pronged approach to mitigate, reduce or treat CRS.

The CD24 protein may be administered simultaneously or metronomically with other treatments. The term "simultaneous" or "simultaneously" as used herein, means that the CD24 protein and other treatment be administered within 48 hours, preferably 24 hours, more preferably 12 hours, yet more preferably 6 hours, and most preferably 3 hours or less, of each other. The term "metronomically" as used herein means the administration of the agent at times different from the other treatment and at a certain frequency relative to repeat administration.

The CD24 protein may be administered at any point prior to another treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins., 5 mins., 4 mins., 3 mins, 2 mins, and 1 mins. The CD24 protein may be administered at any point prior to a second treatment of the CD24 protein including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

The CD24 protein may be administered at any point after another treatment including about 1 min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr. The CD24 protein may be administered at any point prior after a previous CD24 treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

EXAMPLE 1

CD24 Pharmacokinetics in Mice 1 mg of CD24Fc (CD24Fc) was injected into naïve C57BL/6 mice and collected blood samples at different timepoints (5 min, 1 hr, 4 hrs, 24 hrs, 48 hrs, 7 days, 14 days and 21 days) with 3 mice in each timepoint. The sera were diluted 1:100 and the levels of CD24Fc was detected using a sandwich ELISA using purified anti-human CD24 (3.3 µg/ml) as the capturing antibody and peroxidase conjugated goat anti-human IgG Fc (5 µg/ml) as the detecting antibodies. As shown in FIG. 3A. The decay curve of CD24Fc revealed a typical biphase decay of the protein. The first biodistribution phase had a half-life of 12.4 hours. The second phase follows a model of first-order elimination from the central compartment. The half-life for the second phase was 9.54 days, which is similar to that of antibodies in vivo. These data suggest that the fusion protein is very stable in the blood stream. In another study in which the fusion protein was injected subcutaneously, an almost identical half-life of 9.52 days was observed (FIG. 3B). More importantly, while it took approximately 48 hours for the CD24Fc to reach peak levels in the blood, the total amount of the fusion protein in the blood, as measured by AUC, was substantially the same by either route of injection. Thus, from a therapeutic point of view, different route of injection should not affect the therapeutic effect of the drug. This observation greatly simplified the experimental design for primate toxicity and clinical trials.

EXAMPLE 2

CD24-Siglec 10 Interaction in Host Response To Tissue Injuries

Nearly two decades ago, Matzinger proposed what was popularly called danger theory. In essence, she argued that the immune system is turned on when it senses the dangers in the host. Although the nature of danger was not well defined at the time, it has been determined that necrosis is associated with the release of intracellular components such as HMGB1 and Heat-shock proteins, which were called DAMP, for danger-associated molecular patterns. DAMP were found to promote production of inflammatory cytokines and autoimmune diseases. In animal models, inhibitors of HMGB1 and HSP90 were found to ameliorate RA. The involvement of DAMP raised the prospect that negative regulation for host response to DAMP can be explored for RA therapy.

Figure 4:
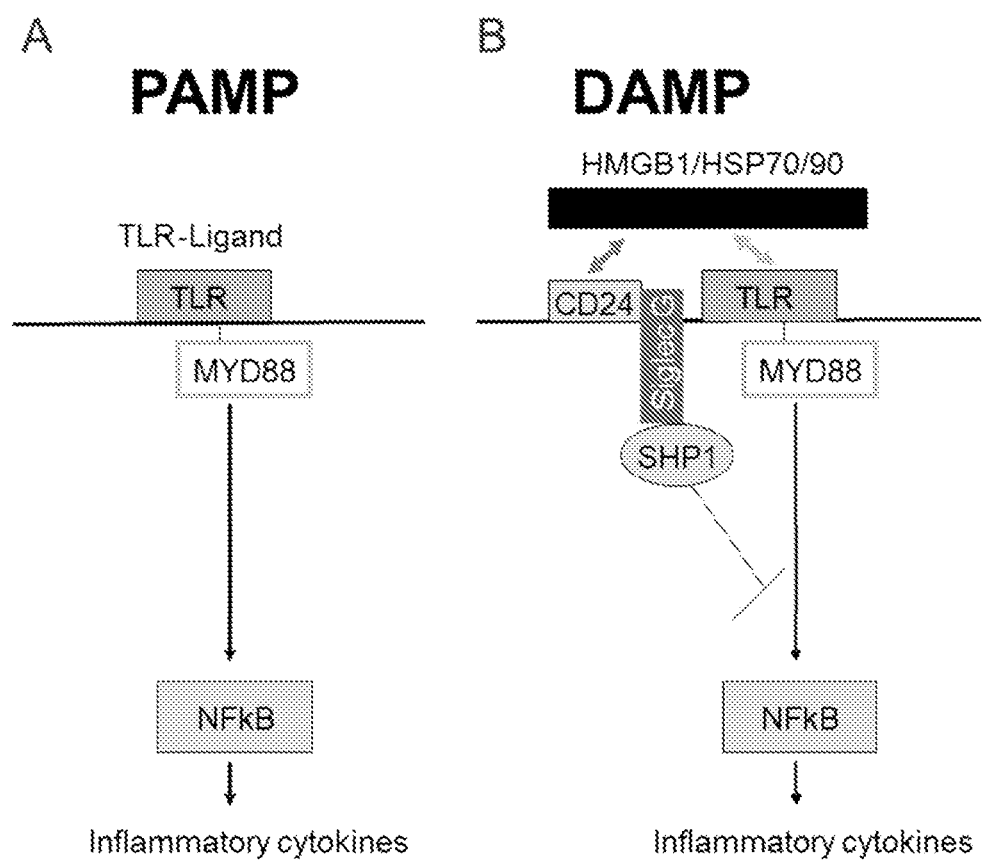
FIG. 4. CD24-Siglec G (10) interaction discriminates between PAMP and DAMP.

Using acetaminophen-induced liver necrosis and ensuring inflammation, it was observed that through interaction Siglec G, CD24 provides a powerful negative regulation for host response to tissue injuries. CD24 is a GPI anchored molecules that is broadly expressed in hematopoietic cells and other tissue stem cells. Genetic analysis of a variety of autoimmune disease in human, including multiple sclerosis, systemic lupus erythromatosus, RA, and giant cell arthritis, showed significant association between CD24 polymorphism and risk of autoimmune diseases. Siglec G is a member of I-lectin family, defined by their ability to recognize sialic acid containing structure. Siglec G recognized sialic acid containing structure on CD24 and negatively regulates production of inflammatory cytokines by dendritic cells. In terms of its ability to interact with CD24, human Siglec 10 and mouse Siglec G are functionally equivalent. However, it is unclear if there is a one-to-one correlation between mouse and human homologues. Although the mechanism remains to be full elucidated, it is plausible that SiglecG-associated SHPT may be involved in the negative regulation. These data, reported in Science recently, leads to a new model in which CD24-Siglec G/10 interaction may play a critical in discrimination pathogen-associated molecular pattern (PAMP) from DAMP (FIG. 4).

At least two overlapping mechanisms may explain the function of CD24. First, by binding to a variety of DAMP, CD24 may trap the inflammatory stimuli to prevent their interaction with TLR or RAGE. This notion is supported by observations that CD24 is associated with several DAMP molecules, including HSP70, 90, HMGB1 and nucleolin. Second, perhaps after associated with DAMP, CD24 may stimulate signaling by Siglec G. Both mechanisms may act in concert as mice with targeted mutation of either gene mounted much stronger inflammatory response. In fact, DC cultured from bone marrow from either CD24−/− or Siglec G−/− mice produced much higher inflammatory cytokines when stimulated with either HMGB1, HSP70, or HSP90. In contrast, no effect were found in their response to PAMP, such as LPS and PolyI:C. These data not only provided a mechanism for the innate immune system to distinguish pathogen from tissue injury, but also suggest that CD24 and Siglec G as potential therapeutic targets for diseases associated with tissue injuries.

EXAMPLE 3

CD24 and the Prevention of GvHD

CD24Fc interacts with HMGB1, Siglec 10 and induces association between Siglec G and SHP-1.

Figure 5A:
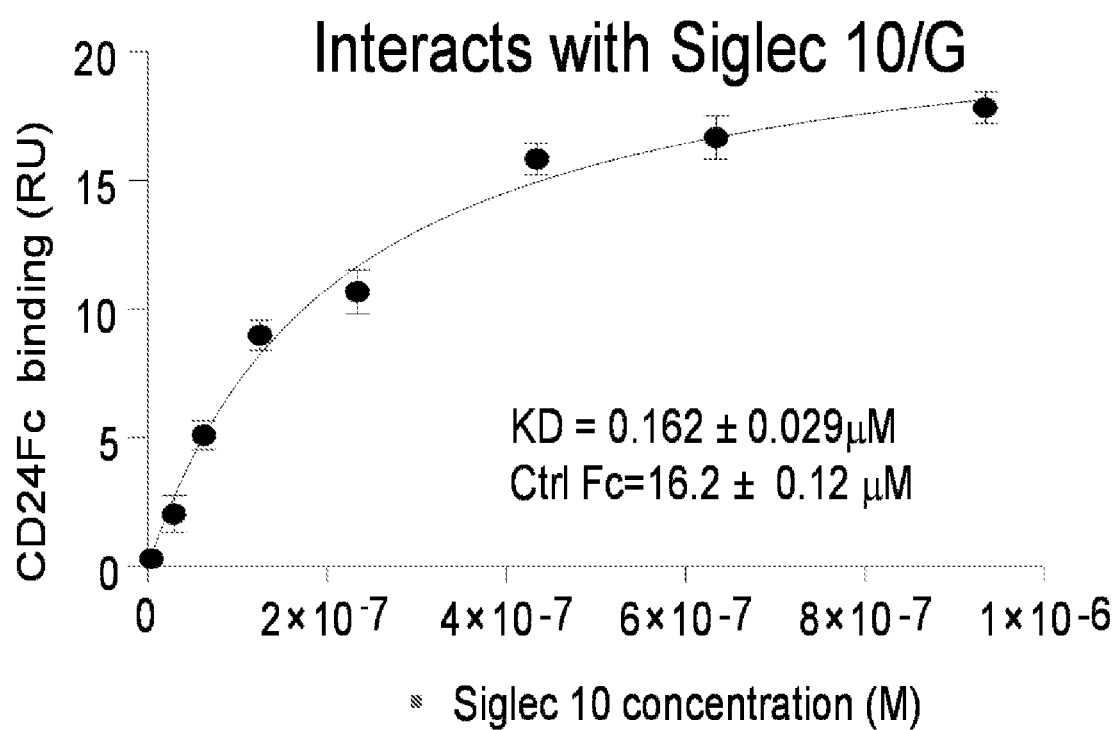
FIG. 5A. Affinity measurement of the CD24-Fc-Siglec 10 interaction.
Figure 5C:
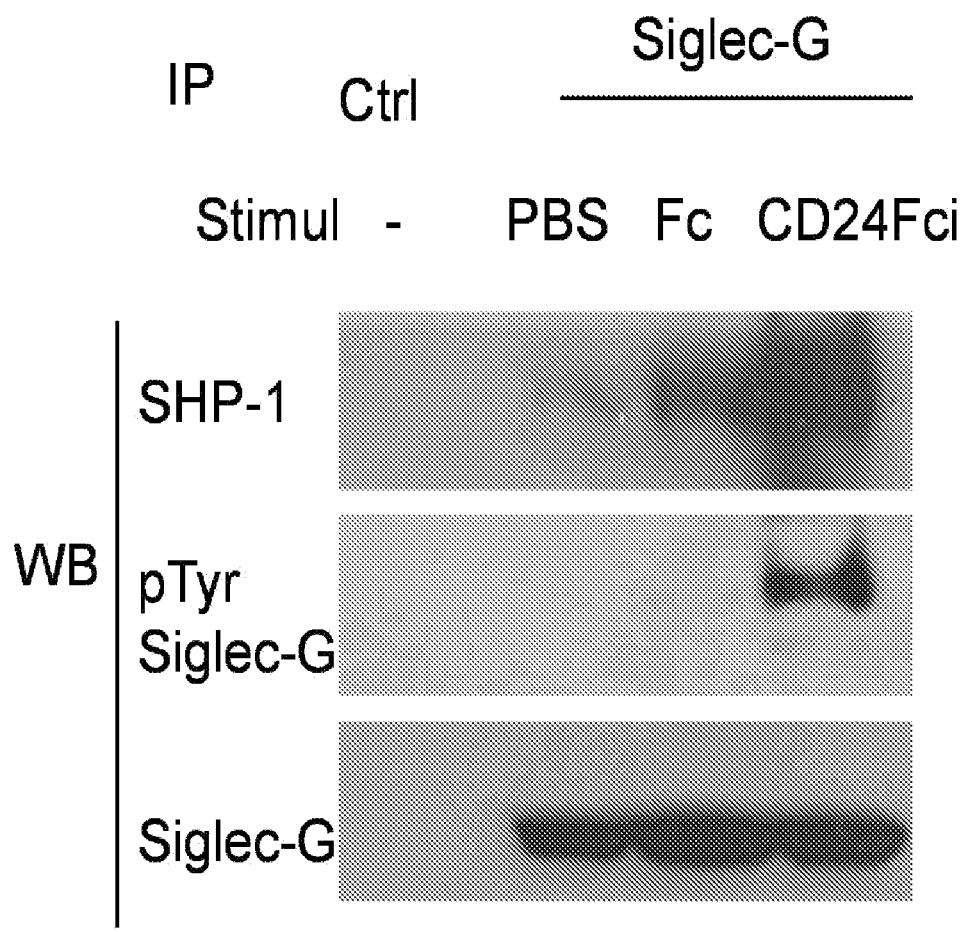
FIG. 5C. CD24-Fc activates mouse Siglec G by inducing Tyrosine phosphorylation (middle panel) and association with SHP-1 (upper panel). The amounts of Siglec G are shown in the lower panel. CD24$^{-/-}$ spleen cells were stimulated with 1 μg/ml of CD24-Fc, control Fc or vehicle (PBS) control for 30 minutes. Siglec G was then immunoprecipitated and probed with anti-phospho-tyrosine or anti-SHP-1.

To measure the interaction between CD24Fc and Siglec 10, we immobilized CD24Fc onto a CHIP and used Biacore to measure the binding of different concentrations of Siglec-10Fc. As shown in FIG. 5A, CD24Fc binds with Siglec 10 with a Kd of $1.6 \times 10^{-7}$ M. This is 100-fold higher affinity than the control Fc. The interaction between CD24Fc and HMGB1 was confirmed by pull down experiments using CD24Fc-bound protein G beads followed by Western blot with either anti-IgG or anti-HMGB1. These data demonstrate that CD24Fc, but not Fc, binds to HMGB1 and that this binding is cation-dependent (FIG. 5B). To determine whether CD24Fc is an agonist of Siglec G, the mouse counterpart of human Siglec 10, we stimulated CD24−/− spleen cells with CD24Fc, control Fc or vehicle (PBS) control for 30 minutes. Siglec G was then immunoprecipitated and probed with anti-phospho-tyrosine or anti-SHP-1. As shown in FIG. 5C, CD24Fc induced substantial phosphorylation of Siglec G and association of SHP-1, a well-known inhibitor for both adaptive and innate immunity.

In vitro efficacy studies of CD24Fc.

Figure 6A:
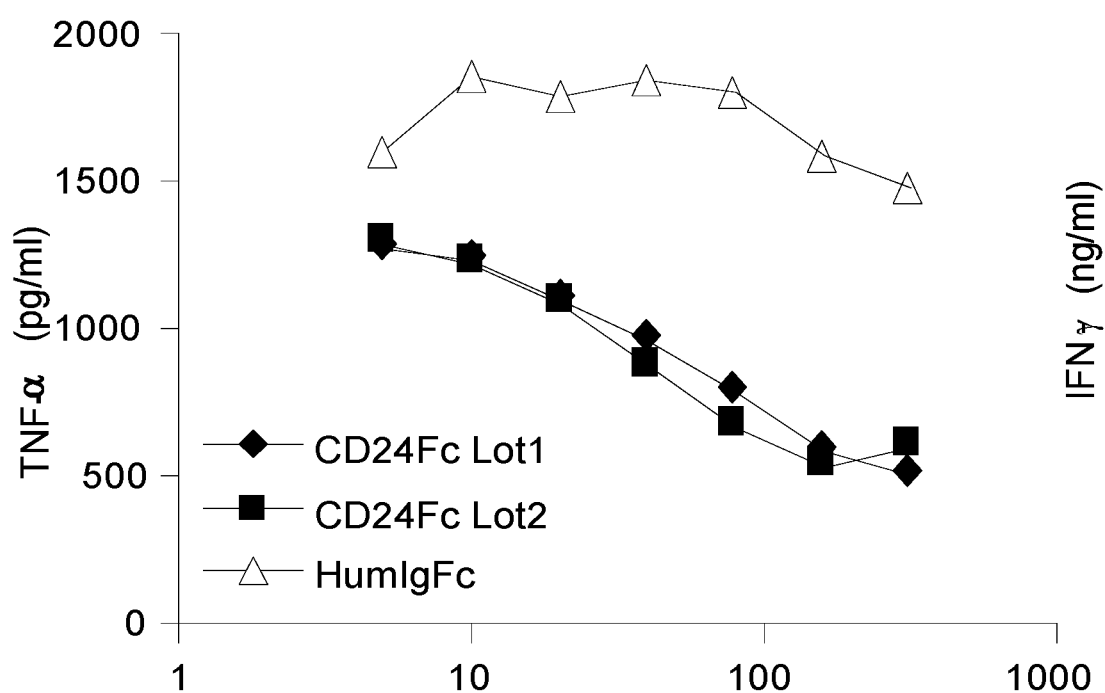
FIG. 6. CD24Fc inhibits production of TNF-α and IFN-γ by anti-CD3 activated human T cells. The human PBML were stimulated with anti-CD3 for 4 days in the presence or absence of CD24Fc and the amounts of IFN-γ and TNF-α released in the supernatant of cell culture were measured by ELISA. Data shown are means of triplicate. Error bar, SEM.
Figure 6B:
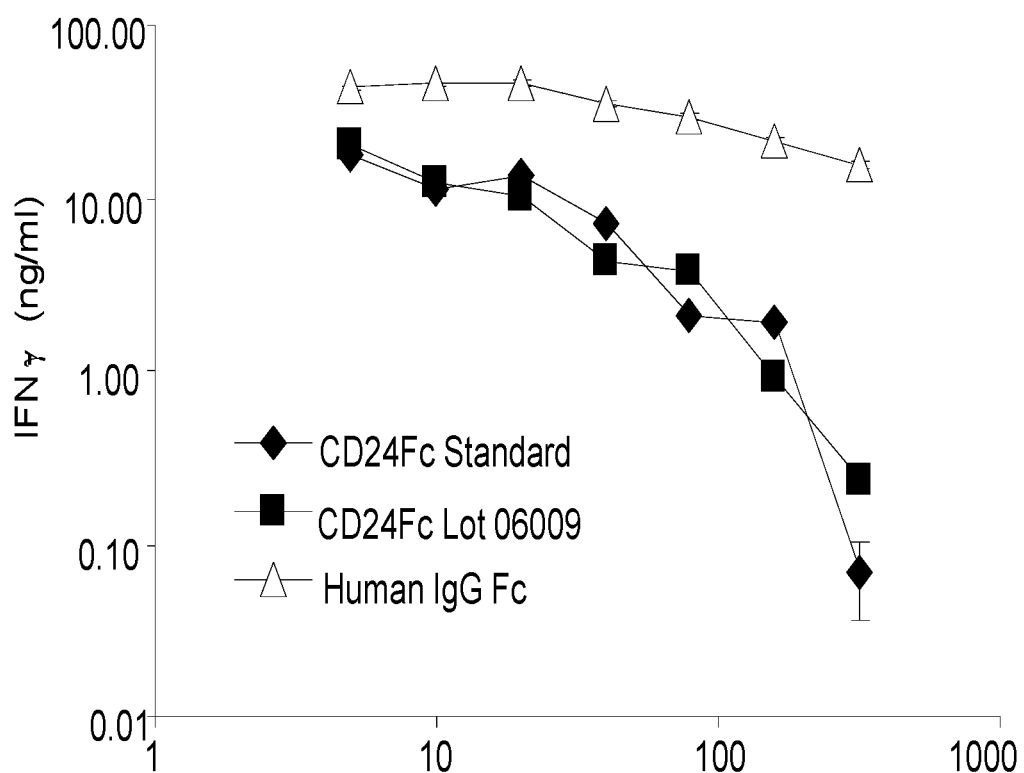

To study the impact of CD24Fc on the production of inflammatory cytokines by human T cells, the mature T cells in human PBML were activated by anti-CD3 antibody (OKT3), a commonly used agonist of the T cell receptor in the presence of different concentrations of CD24Fc or human IgG1 Fc. Four days later, the supernatants were collected and the production of IFN-γ and TNF-α were measured by Enzyme-linked immunosorbent assay (ELISA) to confirm activation. The results in FIG. 6 demonstrated that CD24Fc from two different manufacturing lots significantly reduced IFN-γ and TNF-α production from the activated human PBML compared with control IgG Fc control. In addition, when CD24Fc was added, cytokine production was inhibited in a dose-dependent manner. Therefore, CD24Fc can inhibit anti-CD3 induced human PBML activation in vitro. This study not only indicated the mechanism of action of CD24Fc might be through the inhibition of T cell activation, but also established a reliable bioassay for drug potency and stability testing.

Figure 7:
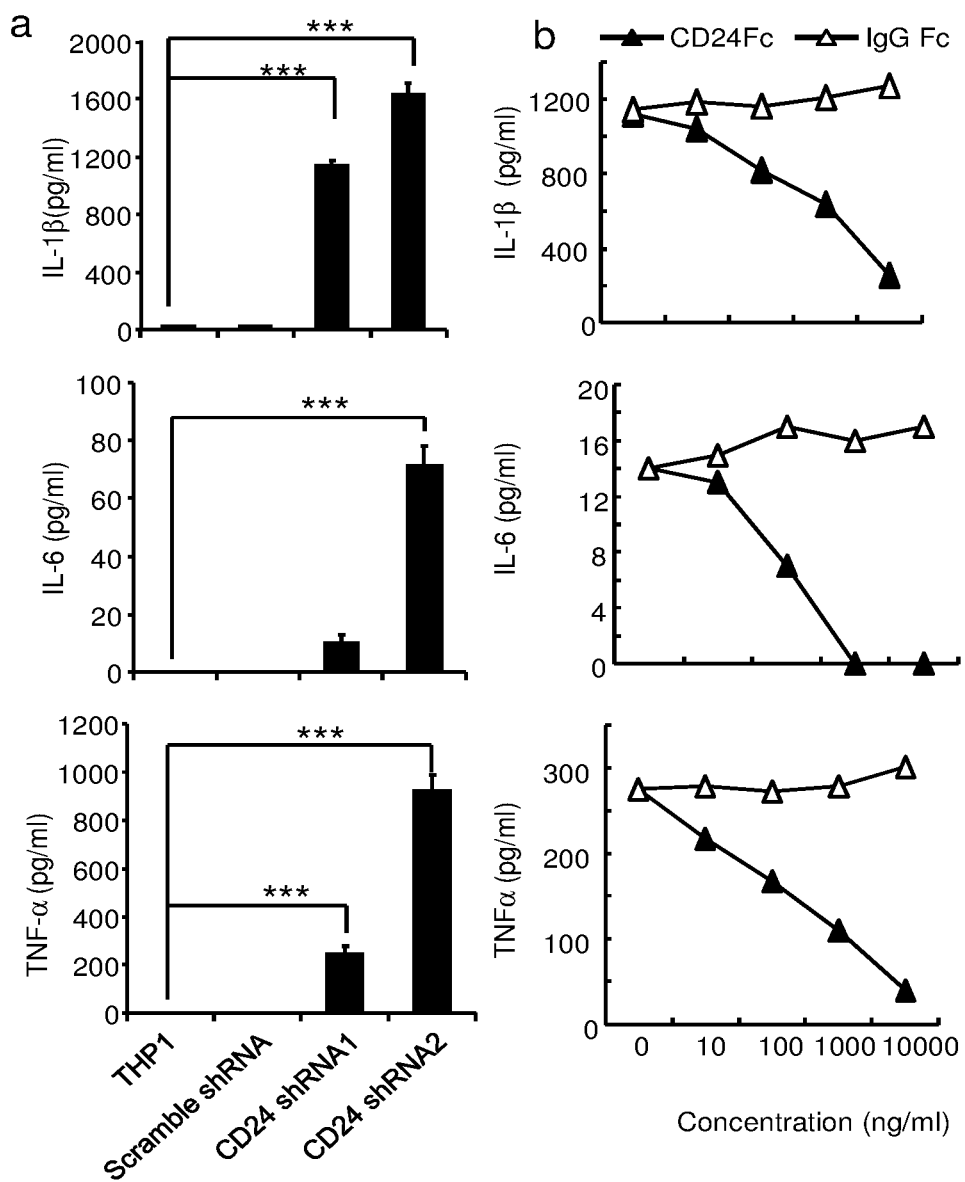
FIG. 7. CD24 inhibits inflammatory cytokine production by human macrophages.

To determine whether CD24Fc regulates production of inflammatory cytokines in a human cell line, we first silenced CD24 in the human acute monocytic leukemia THP1 cell line using RNAi, and then induced differentiation into macrophages by treating them with PMA. As shown in FIG. 7A, CD24 silencing substantially increased the production of TNFα, IL-10 and IL-6. These data demonstrate an essential role for endogenous human CD24 in limiting the production of inflammatory cytokines Importantly, CD24Fc restored inhibition of TNFα in the CD24-silenced cell line (FIG. 7B), as well as IL-1 β and IL-6. These data not only demonstrate the relevance of CD24 in inflammatory response of human cells, but also provides a simple assay to assess biological activity of CD24Fc.

Taken together, these data demonstrate that CD24Fc is capable of inhibiting cytokine production triggered by adaptive and innate stimuli. However, since the drug is much more effective in reducing cytokine production by innate effectors, we consider that the primary mechanism for its prophylactic function is to prevent inflammation triggered by tissue injuries at the early phase of transplantation.

Comparison of therapeutic effect between CsA and CD24Fc in the humanized mouse GvHD model.

GvHD is known as a major complication in allogeneic BM transplantation. However, GvHD induction in all humanized animal models relies on transplantation of a large amount of human PBMCs. Some of these humanized animal models could not achieve the systemic GvHD seen in humans Therefore, a humanized systemic GvHD animal model was developed using one half-million human BM cells in newborn NOD/SCID IL2rγ-null (NSG) mice. The results show that mice developed xenogeneic GvHD with 100% penetrance and all mice displayed high human chimerism as early as 14 days after transplantation which significantly increased to nearly two fold 7 days later (data not shown). The total mortality rate is 100% within 1-2 months of transplantation depending on the donor used (data not shown). Moreover, the human T cells infiltrate multiple target organs, including lung, liver, skin and intestine. To the knowledge of the inventors, this is the best model for pathogenesis of human acute GVHD, but therapeutically more challenging due to severity and rapid onset of the disease.

Figure 8:
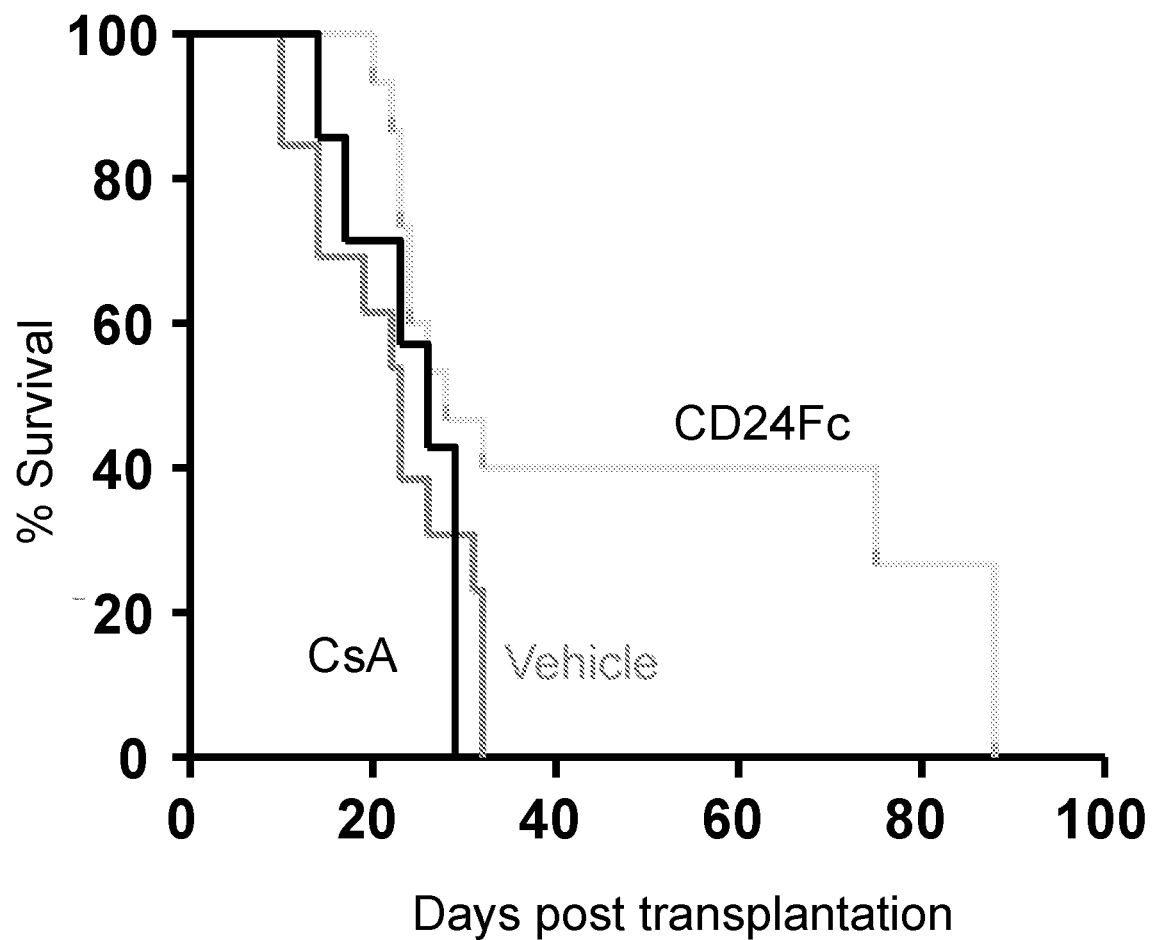
FIG. 8. Kaplan-Meier survival analysis of therapeutic efficacy of CD24Fc and CsA, summary data from two independent experiments.

The donors used for two experiments caused unusually rapid and severe GVHD. To compare the therapeutic efficacies of cyclosporine A (CsA) and CD24Fc, the NSG mice were treated at one week after transplantation with either daily maximal tolerable doses of CsA (between 0.3 and 1 mg/kg for up to 4 weeks, depending on the age of mice) or 2-4 weekly doses of CD24Fc (5 mg/kg). As shown in FIG. 8, starting at the second week, rapid onset of GVHD-related death was observed in the vehicle group. While CD24Fc significantly extended the survival of the recipient mice (P=0.015), CsA failed to significantly extend the survival (P=0.097). These data demonstrate that CD24Fc has superior therapeutic efficacy as compared to CsA.

EXAMPLE 4

CD24 Pharmacokinetics in Humans

This example shows an analysis of the pharmacokinetics of a CD24 protein in humans This was derived from a Phase I, randomized, double-blind, placebo-controlled, single ascending dose study to assess the safety, tolerability, and PK of CD24Fc in healthy male and female adult subjects. A total of 40 subjects in 5 cohorts of 8 subjects each were enrolled in this study. Six of the 8 subjects in each cohort received study drug and 2 subjects received placebo (0.9% sodium chloride, saline). The first cohort was dosed with 10 mg. Succeeding cohorts received 30 mg, 60 mg, 120 mg, and 240 mg of CD24Fc or matching placebo and were dosed at least 3 weeks apart to allow for review of safety and tolerability data for each prior cohort. Administration of the next higher dose to a new cohort of subjects was permitted only if adequate safety and tolerability had been demonstrated.

In each cohort, the initial 2 subjects were 1 study drug recipient and 1 placebo recipient on Day 1. The 3rd to 5th and 6th to 8th subjects were dosed after Day 7 (a minimum of 24 hours apart between the subgroups). Each subject was dosed at least 1 hour apart in the same subgroup. If necessary, dosing of the rest of subjects was delayed pending review of any significant safety issues that may have arisen during the post-dose period involving the first or second subgroups in that cohort. The subsequent cohort was dosed at least 3 weeks after the prior cohort.

Screening Period:

The Screening Visit (Visit 1) occurred up to 21 days prior to the beginning of the active treatment period. After providing informed consent, subjects underwent screening procedures for eligibility.

Treatment Period:

Subjects were admitted to the Clinical Pharmacology Unit (CPU) on Day-1 (Visit 2), and the randomized treatment period began on Day 1 following a 10-hour minimum overnight fast. Subjects were randomly assigned to treatment with CD24Fc or placebo as a single dose. Subjects remained confined until the morning of Day 4.

Follow-up:

All subjects returned to the CPU on Day 7, Day 14, Day 21, Day 28, and Day 42 (±1 day) for follow-up visits (Visit 3, Visit 4, Visit 5, Visit 6, and Visit 7). Visit 7 was the final visit for all subjects.

Duration of Treatment: The total study duration for each subject was up to 63 days. Single-dose administration occurred on Day 1.

Number of Subjects:
Planned: 40 subjects
Screened: 224 subjects
Randomized: 40 subjects
Completed: 39 subjects
Discontinued: 1 subject Diagnosis and Main Criteria for Inclusion: The population for this study was healthy males and females between the ages of 18 and 55 years, inclusive, with a body mass index between 18 kg/m$^2$ and 30 kg/m$^2$, inclusive.

Investigational Product and Comparator Information:

CD24Fc: single dose of 10 mg, 30 mg, 60 mg, 120 mg, or 240 mg administered via IV infusion; lot number: 09MM-036. CD24Fc was a fully humanized fusion protein consisting of the mature sequence of human CD24 and the fragment crystallizable region of human immunoglobulin G1 (IgG1Fc). CD24Fc was supplied as a sterile, clear, colorless, preservative-free, aqueous solution for IV administration. CD24Fc was formulated as single dose injection solution, at a concentration of 10 mg/mL and a pH of 7.2. Each CD24Fc vial contained 160 mg of CD24Fc, 5.3 mg of sodium chloride, 32.6 mg of sodium phosphate dibasic heptahydrate, and 140 mg of sodium phosphate monobasic monohydrate in 16 mL±0.2 mL of CD24Fc. CD24Fc was supplied in clear borosilicate glass vials with chlorobutyl rubber stoppers and aluminum flip-off seals.

Matching placebo (0.9% sodium chloride, saline) administered via IV infusion; lot numbers: P296855, P311852, P300715, P315952.

The intent-to-treat (ITT) Population consisted of all subjects who received at least 1 dose of the study drug. The ITT Population was the primary analysis population for subject information and safety evaluation.

Clinical laboratory evaluations (chemistry, hematology, and urinalysis) were summarized by treatment and visit. Change from baseline was also summarized. Vital signs (blood pressure, heart rate, respiratory rate, and temperature) were summarized by treatment and time point. Change from baseline was also summarized. All physical examination data were listed. Electrocardiogram parameters and the change from baseline were summarized. Overall interpretations were listed.

Plasma CD24Fc Concentration

Figure 9:
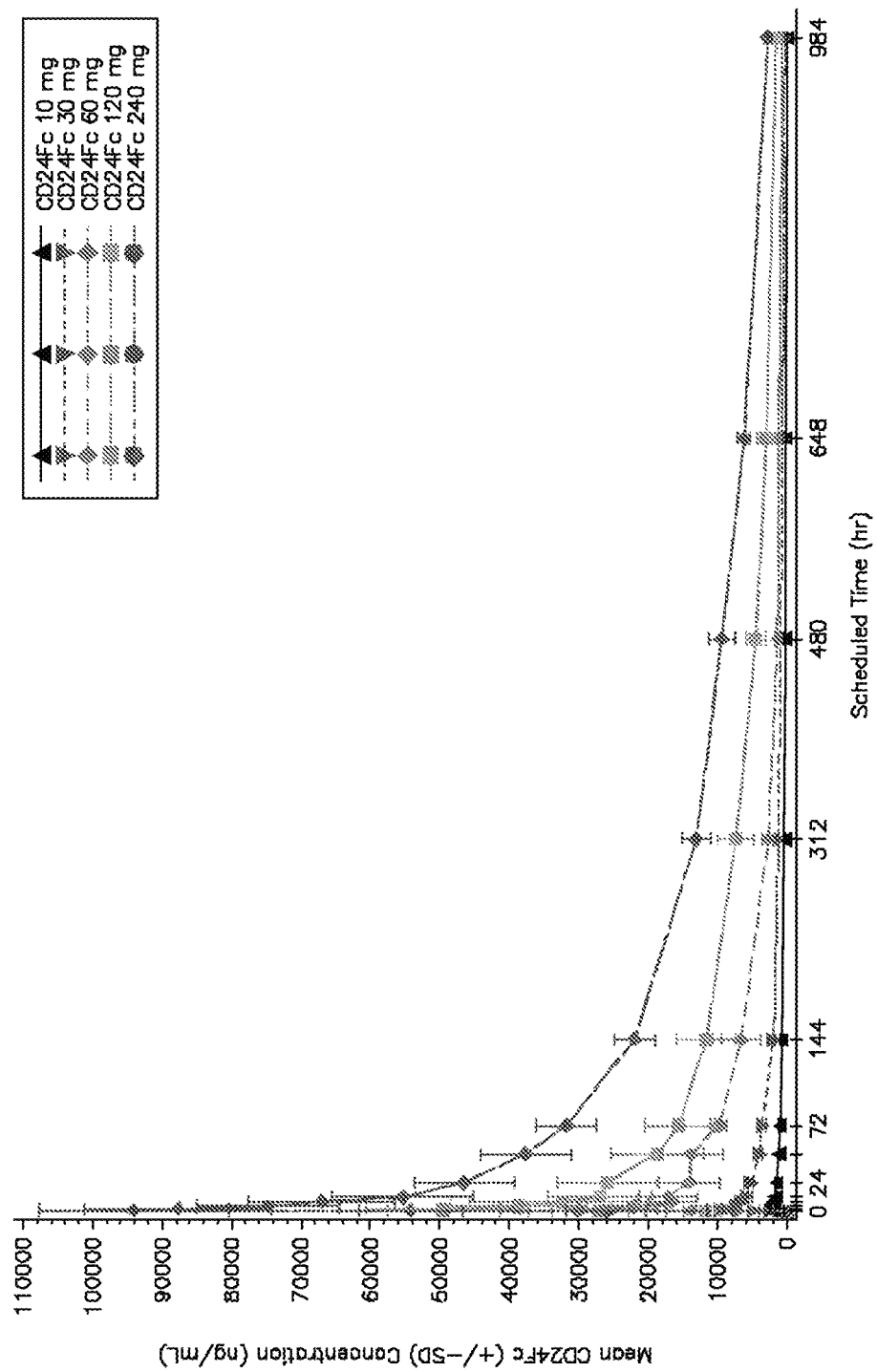
FIG. 9 shows a plot of mean plasma CD24Fc concentration (±SD) by treatment for a PK Evaluable Population in human subjects. PK=pharmacokinetic; SD=standard deviation.

As shown in FIG. 9, the mean plasma concentration of CD24Fc increased proportionally to the dose of CD24Fc administered. For all dose groups except 120 mg, the maximum mean plasma concentration of CD24Fc was reached at 1 hour post-dose. The maximum mean plasma concentration of CD24Fc for the 120 mg group was reached at 2 hours post-dose. By Day 42 (984 hours), the mean plasma concentration of CD24Fc for all groups had decreased to between 2% and 4% of the maximum mean plasma concentration.

Table 1 summarizes the plasma CD24Fc PK parameters by treatment for the PK Evaluable Population.

TABLE 1

Summary of Plasma CD24Fc Pharmacokinetic Parameters by Treatment-PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) |
|---|---|---|---|---|---|
| $C_{max}$ (ng/mL) | | | | | |
| n | 6 | 6 | 6 | 6 | 6 |
| Mean (SD) | 2495 (576) | 9735 (1715) | 30 083 (7179) | 52 435 (9910) | 95 865 (10 734) |
| CV % | 23.1 | 17.6 | 23.9 | 18.9 | 11.2 |
| Median | 2371 | 9218 | 29 026 | 50 401 | 93 206 |
| Min, Max | 1,967, 3,390 | 8,583, 13,086 | 22,557, 42,628 | 40,434, 65,704 | 81,296, 110,110 |
| Geometric mean | 2,442 | 9,625 | 29,424 | 51,666 | 95,365 |
| Geometric CV % | 22.8 | 16.1 | 23.0 | 19.0 | 11.2 |
| $AUC_{0-42d}$ (ng*hr/mL) | | | | | |
| n | 6 | 6 | 6 | 6 | 6 |
| Mean (SD) | 423,061 (99,615) | 1,282,430 (88,798) | 3,226,255 (702,862) | 6,541,501 (2,190,944) | 12,704,705 (1,918,596) |
| CV % | 23.5 | 6.9 | 21.8 | 33.5 | 15.1 |
| Median | 434,043 | 1,302,719 | 3,124,933 | 5,785,142 | 12,563,426 |
| Min, Max | 291,020, 528,079 | 1,175,733, 1,403,024 | 2,487,550, 4,139,748 | 4,485,193, 9,415,266 | 10,466,635, 15,693,606 |
| Geometric mean | 412,795 | 1,279,851 | 3,163,252 | 6,249,552 | 12,586,731 |
| Geometric CV % | 25.0 | 7.0 | 22.0 | 33.8 | 15.0 |

TABLE 1-continued

Summary of Plasma CD24Fc Pharmacokinetic Parameters by Treatment-
PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) |
|---|---|---|---|---|---|
| $AUC_{0\text{-}inf}$ (ng*hr/mL) | | | | | |
| n | 6 | 6 | 6 | 6 | 6 |
| Mean (SD) | 462,260 (116,040) | 1,434,464 (131,316) | 3,497,196 (705,653) | 7,198,196 (2,458,320) | 13,861,796 (1,962,780) |
| CV % | 25.1 | 9.2 | 20.2 | 34.2 | 14.2 |
| Median | 470,426 | 1,422,205 | 3,519,732 | 6,463,665 | 13,713,034 |
| Min, Max | 310,956, 596,599 | 1,281,715, 1,650,503 | 2,703,655, 4,309,023 | 4,910,640, 10,479,940 | 11,822,988, 17,175,236 |
| Geometric mean | 449,583 | 1,429,578 | 3,437,036 | 6,862,129 | 13,750,972 |
| Geometric CV % | 26.7 | 9.0 | 20.7 | 34.6 | 13.8 |
| $T_{max}$ (hr) | | | | | |
| n | 6 | 6 | 6 | 6 | 6 |
| Mean (SD) | 1.15 (0.42) | 1.17 (0.41) | 1.01 (0.01) | 1.34 (0.51) | 1.33 (0.52) |
| CV % | 36.1 | 35.0 | 1.2 | 38.0 | 38.7 |
| Median | 1.00 | 1.00 | 1.00 | 1.03 | 1.00 |
| Min, Max | 0.92, 2.00 | 1.00, 2.00 | 1.00, 1.03 | 1.00, 2.00 | 1.00, 2.00 |
| $t\frac{1}{2}$ (hr) | | | | | |
| n | 6 | 6 | 6 | 6 | 6 |
| Mean (SD) | 280.83 (22.37) | 327.10 (41.32) | 279.82 (65.59) | 286.45 (23.38) | 285.33 (24.33) |
| CV % | 8.0 | 12.6 | 23.4 | 8.2 | 8.5 |
| Median | 279.61 | 317.23 | 264.69 | 290.76 | 287.74 |
| Min, Max | 258.87, 321.26 | 289.82, 394.24 | 210.18, 362.46 | 243.89, 309.26 | 249.24, 322.26 |
| AUCextr (%) | | | | | |
| n | 6 | 6 | 6 | 6 | 6 |
| Mean (SD) | 7.61 (2.14) | 10.44 (2.94) | 7.88 (4.26) | 8.92 (1.94) | 8.46 (1.99) |
| CV % | 28.1 | 28.2 | 54.0 | 21.8 | 23.5 |
| Median | 7.16 | 10.01 | 6.35 | 9.27 | 8.45 |
| Min, Max | 5.46, 11.47 | 7.10, 15.05 | 3.92, 14.48 | 5.49, 10.99 | 5.56, 11.50 |
| CL (L/hr) | | | | | |
| n | 6 | 6 | 6 | 6 | 6 |
| Mean (SD) | 0.0229 (0.0061) | 0.0211 (0.0019) | 0.0178 (0.0036) | 0.0183 (0.0058) | 0.0176 (0.0023) |
| CV % | 26.7 | 8.8 | 20.5 | 31.7 | 13.3 |
| Median | 0.0216 | 0.0211 | 0.0173 | 0.0191 | 0.0175 |
| Min, Max | 0.0168, 0.0322 | 0.0182, 0.0234 | 0.0139, 0.0222 | 0.0115, 0.0244 | 0.0140, 0.0203 |
| Vd (L) | | | | | |
| n | 6 | 6 | 6 | 6 | 6 |
| Mean (SD) | 9.153 (1.943) | 9.867 (0.804) | 7.289 (2.592) | 7.491 (2.202) | 7.276 (1.426) |
| CV % | 21.2 | 8.1 | 35.6 | 29.4 | 19.6 |
| Median | 8.507 | 10.007 | 7.486 | 7.691 | 7.151 |
| Min, Max | 7.326, 12.010 | 8.771, 10.958 | 4.222, 11.139 | 4.933, 9.974 | 5.814, 9.438 |

$AUC_{0\text{-}42d}$ = area under the concentration-time curve from time 0 to 42 days; $AUC_{0\text{-}inf}$ = area under the concentration-time curve extrapolated from time 0 to infinity; $AUC_{extr}$ = percentage of $AUC_{0\text{-}inf}$ that was due to the extrapolation from the time of the last measurable concentration, per subject, to infinity; CL = total body clearance; $C_{max}$ = maximum observed plasma drug concentration; CV % = coefficient of variation; Min = minimum; Max = maximum; SD = standard deviation; $t_{1/2}$ = terminal elimination half-life; $T_{max}$ = time of maximum observed plasma drug concentration; $V_d$ = volume of distribution.

Plasma CD24Fc Dose Proportionality Analysis

Figure 10:
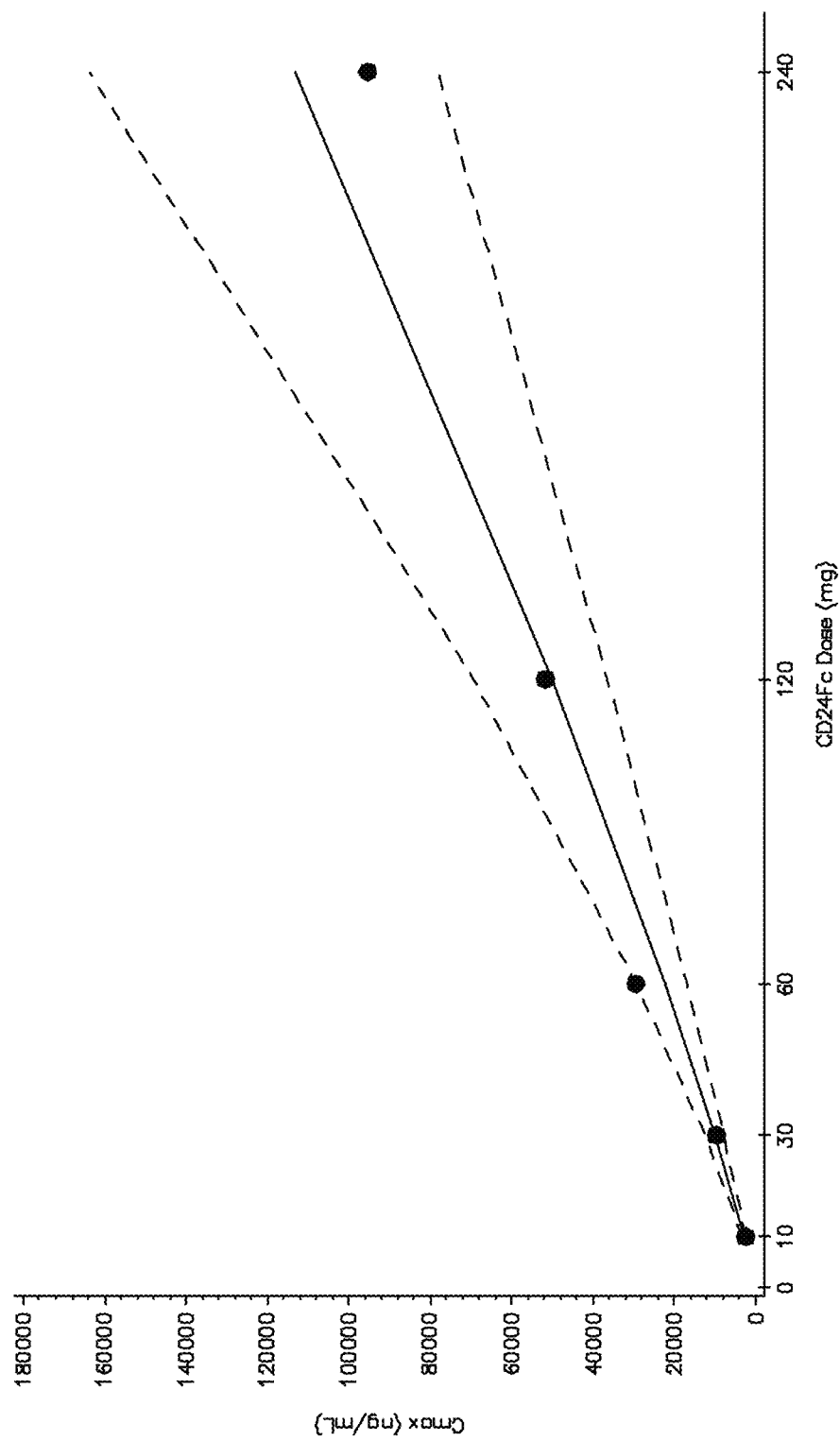
FIG. 10 shows a dose proportionality plot of CD24Fc $C_{max}$, versus dose for a PK Evaluable Population.
Figure 11:
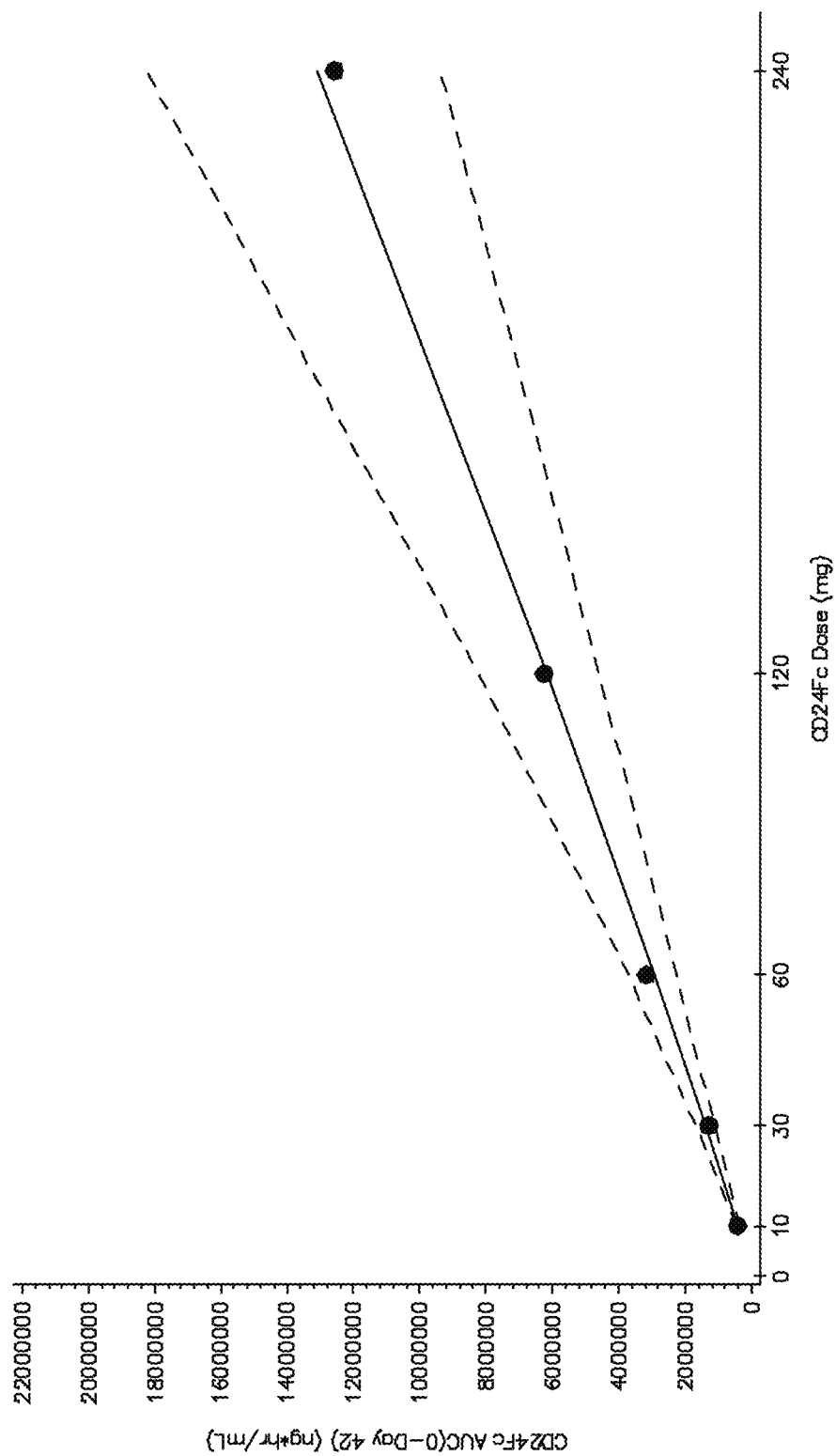
FIG. 11 shows a dose proportionality plot of CD24Fc $AUC_{0-42}$ versus dose for a PK Evaluable Population.
Figure 12:
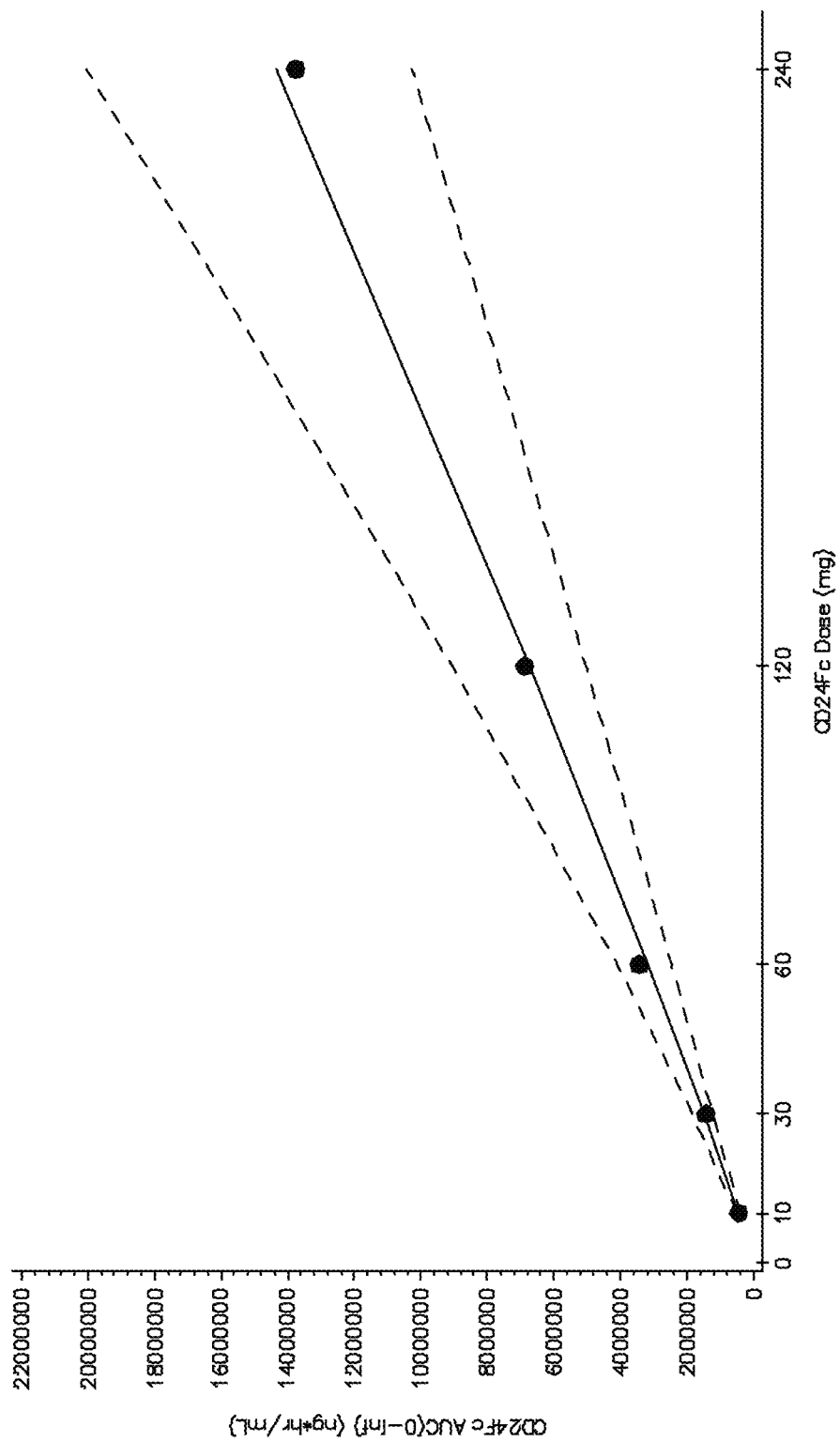
FIG. 12 shows a dose proportionality plot of CD24Fc $AUC_{0-inf}$ versus dose for a PK Evaluable Population.

FIG. 10 shows a dose proportionality plot of CD24Fc $C_{max}$ versus dose for the PK Evaluable Population. FIG. 11 shows a dose proportionality plot of CD24Fc $AUC_{0\text{-}42d}$ versus dose for the PK Evaluable Population. FIG. 12 shows a dose proportionality plot of CD24Fc $AUC_{0\text{-}inf}$ versus dose for the PK Evaluable Population. Table 2 shows a power analysis of dose proportionality.

TABLE 2

Power Analysis of Dose Proportionality: Plasma CD24Fc Pharmacokinetic Parameters - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) | Dose Proportionality | | |
|---|---|---|---|---|---|---|---|---|
| | | | | | | Slope Estimate | Standard Error | 90% CI |
| $C_{max}$ (ng/mL) Geometric mean | 2,441.8 | 9,624.9 | 29,424.4 | 51,666.4 | 95,364.9 | 1.172 | 0.040 | (1.105, 1.240) |

TABLE 2-continued

Power Analysis of Dose Proportionality: Plasma CD24Fc Pharmacokinetic Parameters - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) | Dose Proportionality | | |
|---|---|---|---|---|---|---|---|---|
| | | | | | | Slope Estimate | Standard Error | 90% CI |
| Geometric CV% | 22.8 | 16.1 | 23.0 | 19.0 | 11.2 | | | |
| $AUC_{0-42d}$ (ng * hr/mL) | | | | | | 1.088 | 0.036 | (1.027, 1.148) |
| Geometric mean | 412,794.8 | 1,279,850.8 | 3,163,251.7 | 6,249,551.9 | 12,586,731.3 | | | |
| Geometric CV% | 25.0 | 7.0 | 22.0 | 33.8 | 15.0 | | | |
| $AUC_{0-inf}$ (ng * hr/mL) | | | | | | 1.087 | 0.036 | (1.026, 1.148) |
| Geometric mean | 449,583.5 | 1,429,577.5 | 3,437,035.6 | 6,862,128.7 | 13,750,972.4 | | | |
| Geometric CV% | 26.7 | 9.0 | 20.7 | 34.6 | 13.8 | | | |

Geometric CV% = 100 * sqrt(exp($SD^2$) − 1), where SD was the standard deviation of the log-transformed data. The power model was fitted by restricted maximum likelihood, regressing the log-transformed PK parameter on log transformed dose. Both the intercept and slope were fitted as fixed effects. Dose proportionality was not rejected if the 90% CI lies within (0.8, 1.25).
$AUC_{0-42d}$ = area under the concentration-time curve from time 0 to 42 days; $AUC_{0-inf}$ = area under the concentration-time curve extrapolated from time 0 to infinity;
CI = confidence interval; $C_{max}$ = maximum observed plasma drug concentration; CV% = coefficient of variation; PK = pharmacokinetic; SD = standard deviation.

The $C_{max}$ slope estimate was 1.172 with a 90% CI of 1.105 to 1.240. The $AUC_{0-42d}$ slope estimate was 1.088 with a 90% CI of 1.027 to 1.148. The $AUC_{0-inf}$ slope estimate was 1.087 with a 90% CI of 1.026 to 1.1.

Pharmacokinetic Conclusions

The $C_{max}$ and AUCs of plasma CD24Fc increased proportionally to the doses administered in mouse, monkey and human The plasma CD24Fc reached $T_{max}$ between 1.01 and 1.34 hours. The $t^{1/2}$ of plasma CD24Fc ranged between 280.83 and 327.10 hours.

REFERENCES

1. Munoz L E, Janko C, Schulze C, Schorn C, Sarter K, Schett G, Herrmann M. Autoimmunity and chronic inflammation—two clearance-related steps in the etiopathogenesis of SLE. Autoimmun Rev. 2010; 10(1): 38-42. Epub 2010/09/08. doi: 10.1016/j.autrev.2010.08.015. PubMed PMID: 20817127.
2. Urbonaviciute V, Furnrohr B G, Meister S, Munoz L, Heyder P, De Marchis F, Bianchi M E,
Kirschning C, Wagner H, Manfredi A A, Kalden J R, Schett G, Rovere-Querini P, Herrmann M, Voll R E. Induction of inflammatory and immune responses by HMGB1-nucleosome complexes: implications for the pathogenesis of SLE. J Exp Med. 2008; 205(13):3007-18. PubMed PMID: 19064698.
3. Wen Z, Xu L, Chen X, Xu W, Yin Z, Gao X, Xiong S. Autoantibody induction by DNA-containing immune complexes requires HMGB1 with the TLR2/microRNA-155 pathway. Journal of Immunology. 2013; 190(11): 5411-22. Epub 2013/04/26. doi: 10.4049/jimmunol.1203301. PubMed PMID: 23616573.
4. Andersson U, Harris H E. The role of HMGB1 in the pathogenesis of rheumatic disease. Biochim Biophys Acta.1799(1-2):141-8. PubMed PMID: 20123076.
5. Ostberg T, Kawane K, Nagata S, Yang H, Chavan S, Klevenvall L, Bianchi M, Harris H E, Andersson U, Palmblad K. Protective targeting of HMGB1 in a spontaneous arthritis model. Arthritis Rheum. 2010; 62:2963-72. PubMed PMID: 20533288.
6. Rice J W, Veal J M, Fadden R P, Barabasz A F, Partridge J M, Barta T E, Dubois L G, Huang K H, Mabbett S R, Silinski M A, Steed P M, Hall S E. Small molecule inhibitors of Hsp90 potently affect inflammatory disease pathways and exhibit activity in models of rheumatoid arthritis. Arthritis Rheum. 2008; 58(12):3765-75. PubMed PMID: 19035474.
7. Ahrens S, Zelenay S, Sancho D, Hanc P, Kjaer S, Feest C, Fletcher G, Durkin C, Postigo A, Skehel M, Batista F, Thompson B, Way M, Reis e Sousa C, Schulz O. F-actin is an evolutionarily conserved damage-associated molecular pattern recognized by DNGR-1, a receptor for dead cells. Immunity. 2012; 36(4):635-45. Epub 2012/04/10. doi: 51074-7613(12)00126-4 [pii]
10.1016/j.immuni.2012.03.008. PubMed PMID: 22483800.
8. Yamasaki S, Ishikawa E, Sakuma M, Hara H, Ogata K, Saito T. Mincle is an ITAM-coupled activating receptor that senses damaged cells. Nat Immunol. 2008; 9(10): 1179-88. Epub 2008/09/09. doi: ni.1651 [pii]
10.1038/ni.1651. PubMed PMID: 18776906.
9. Cavassani K A, Ishii M, Wen H, Schaller M A, Lincoln P M, Lukacs N W, Hogaboam C M, Kunkel SL. TLR3 is an endogenous sensor of tissue necrosis during acute inflammatory events. Journal of Experimental Medicine. 2008; 205(11):2609-21. PubMed PMID: 18838547.
10. Ivanov S, Dragoi A M, Wang X, Dallacosta C, Louten J, Musco G, Sitia G, Yap G S, Wan Y, Biron C A, Bianchi M E, Wang H, Chu W M. A novel role for HMGB1 in TLR9-mediated inflammatory responses to CpG-DNA. Blood. 2007; 110(6):1970-81. Epub 2007/06/06. doi: blood-2006-09-044776 [pii]
10.1182/blood-2006-09-044776. PubMed PMID: 17548579; PMCID: 1976374.
11. Sims G P, Rowe D C, Rietdijk S T, Herbst R, Coyle A J. HMGB1 and RAGE in inflammation and cancer. Annu Rev Immuno1.28:367-88. PubMed PMID: 20192808.
12. van Beijnum J R, Buurman W A, Griffioen A W. Convergence and amplification of toll-like receptor (TLR) and receptor for advanced glycation end products (RAGE) signaling pathways via high mobility group Bi (HMGB1). Angiogenesis. 2008; 11(1):91-9. PubMed PMID: 18264787.
13. Warger T, Hilf N, Rechtsteiner G, Haselmayer P, Carrick D M, Jonuleit H, von Landenberg P, Rammensee H G, Nicchitta C V, Radsak M P, Schild H. Interaction of TLR2 and TLR4 ligands with the N-terminal domain of Gp96 amplifies innate and adaptive immune responses. The Journal of biological chemistry. 2006; 281(32):22545-53. PubMed PMID: 16754684.

14. Zhang Q, Raoof M, Chen Y, Sumi Y, Sursal T, Junger W, Brohi K, Itagaki K, Hauser C J. Circulating mitochondrial DAMPs cause inflammatory responses to injury. Nature. 2010; 464(7285):104-7. Epub 2010/03/06. doi: nature08780 [pii] 10.1038/nature08780. PubMed PMID: 20203610; PMCID: 2843437.
15. Chen G Y, Tang J, Zheng P, Liu Y. CD24 and Siglec-10 selectively repress tissue damage-induced immune responses. Science. 2009; 323(5922):1722-5. doi: 10.1126/science.1168988. PubMed PMID: 19264983; PMCID: PMC2765686.
16. Chen G Y, Chen X, King S, Cavassani K A, Cheng J, Zheng X, Cao H, Yu H, Qu J, Fang D, Wu W, Bai X F, Liu J Q, Woodiga S A, Chen C, Sun L, Hogaboam C M, Kunkel S L, Zheng P, Liu Y. Amelioration of sepsis by inhibiting sialidase-mediated disruption of the CD24-SiglecG interaction. Nat Biotechnol. 2011; 29(5):428-35. doi: 10.1038/nbt.1846. PubMed PMID: 21478876; PMCID: PMC4090080.
17. Chen W, Han C, Xie B, Hu X, Yu Q, Shi L, Wang Q, Li D, Wang J, Zheng P, Liu Y, Cao X. Induction of Siglec-G by RNA viruses inhibits the innate immune response by promoting RIG-I degradation. Cell. 2013; 152(3):467-78. Epub 2013/02/05. doi: 10.1016/j.cell.2013.01.011. PubMed PMID: 23374343.
18. Goris A, Maranian M, Walton A, Yeo T W, Ban M, Gray J, Dubois B, Compston A, Sawcer S. CD24 Ala/Val polymorphism and multiple sclerosis. Journal of neuroimmunology. 2006. PubMed PMID: 16631259.
19. Otaegui D, Saenz A, Camano P, Blazquez L, Goicoechea M, Ruiz-Martinez J, Olaskoaga J, Emparanza J A, Lopez de Munain A. CD24 V/V is an allele associated with the risk of developing multiple sclerosis in the Spanish population. Multiple sclerosis (Houndmills, Basingstoke, England). 2006; 12(4):511-4. Epub 2006/08/12. PubMed PMID: 16900767.
20. Wang L, Lin S, Rammohan K, Liu Z, Liu J, Liu R-H, Guinther N, Zhou Q, Wang T, Zheng X, Birmingham D J, Rovin B H, Herbert L A, Wu Y, Lynn D J, Cooke G, Yu C Y, Zheng P, Liu Y. A di-nucleotide deletion in CD24 confers protection against autoimmune diseases. Plos Genetics. 2007; 3:e49.
21. Zhou Q, Rammohan K, Lin S, Robinson N, Li O, Liu X, Bai X F, Yin L, Scarberry B, Du P, You M, Guan K, Zheng P, Liu Y. CD24 is a genetic modifier for risk and progression of multiple sclerosis. Proc Natl Acad Sci USA. 2003; 100(25):15041-6. doi: 10.1073/pnas.2533866100. PubMed PMID: 14657362; PMCID: PMC299898.
22. Sanchez E, Abelson A K, Sabio J M, Gonzalez-Gay M A, Ortego-Centeno N, Jimenez-Alonso J, de Ramon E, Sanchez-Roman J, Lopez-Nevot M A, Gunnarsson I, Svenungsson E, Sturfelt G, Truedsson L, Jonsen A, Gonzalez-Escribano M F, Witte T, Alarcon-Riquelme M E, Martin J. Association of a CD24 gene polymorphism with susceptibility to systemic lupus erythematosus. Arthritis Rheum. 2007; 56(9):3080-6. Epub 2007/09/01. doi: 10.1002/art.22871. PubMed PMID: 17763438.
23. Sanchez E, Fernandez-Gutierrez B, Gonzalez-Gay M A, Balsa A, Garcia A, Rodriguez L, Pascual-Salcedo D, Gonzalez-Escribano M F, Martin J. Investigating the role of CD24 gene polymorphisms in rheumatoid arthritis. Annals of the rheumatic diseases. 2008; 67(8):1197-8. Epub 2008/07/16. doi: 10.1136/ard.2007.084475. PubMed PMID: 18621973.
24. Rueda B, Miranda-Filloy J A, Martin J, Gonzalez-Gay M A. Association of CD24 gene polymorphisms with susceptibility to biopsy-proven giant cell arteritis. The Journal of rheumatology. 2008; 35(5):850-4. Epub 2008/04/03. PubMed PMID: 18381780.
25. Lee Y H, Bae S C. Association between functional CD24 polymorphisms and susceptibility to autoimmune diseases: A meta-analysis. Cell Mol Biol (Noisy-le-grand). 2015; 61(8):97-104. Epub 2016/01/01. PubMed PMID: 26718436.
26. Bokers S, Urbat A, Daniel C, Amann K, Smith K G, Espeli M, Nitschke L. Siglec-G deficiency leads to more severe collagen-induced arthritis and earlier onset of lupus-like symptoms in MRL/lpr mice. Journal of immunology (Baltimore, Md.: 1950). 2014; 192(7):2994-3002. Epub 2014/03/07. doi: 10.4049/jimmunol.1303367. PubMed PMID: 24600033.
27. Wigren M, Nilsson J, Kaplan M J. Pathogenic immunity in systemic lupus erythematosus and atherosclerosis: common mechanisms and possible targets for intervention. Journal of internal medicine. 2015; 278(5):494-506. Epub 2015/02/28. doi: 10.1111/joim.12357. PubMed PMID: 25720452; PMCID: PMC4550575.
28. Kay R, Rosten P M, Humphries R K, CD24, a signal transducer modulating B cell activation responses, is a very short peptide with a glycosyl phosphatidylinositol membrane anchor. Journal of immunology (Baltimore, Md.: 1950). 1991; 147(4):1412-6. Epub 1991/08/15. PubMed PMID: 1831224.
29. Perry D, Sang A, Yin Y, Zheng Y Y, Morel L. Murine models of systemic lupus erythematosus. Journal of biomedicine & biotechnology. 2011; 2011:271694. Epub 2011/03/16. doi: 10.1155/2011/271694. PubMed PMID: 21403825; PMCID: PMC3042628.
30. Ge Y, Jiang C, Sung S S, Bagavant H, Dai C, Wang H, Kannapell C C, Cathro H P, Gaskin F, Fu S M. Cgnz1 allele confers kidney resistance to damage preventing progression of immune complex-mediated acute lupus glomerulonephritis. J Exp Med. 2013; 210(11):2387-401. Epub 2013/10/09. doi: 10.1084/jem.20130731. PubMed PMID: 24101379; PMCID: PMC3804943.

The invention claimed is:

1. A method of treating immune-related adverse events (irAEs) associated with a cancer therapy in a subject in need thereof, comprising administering to the subject a CD24 protein comprising a mature soluble human CD24 comprising an amino acid sequence set forth in SEQ ID NO: 1, wherein the cancer therapy is selected from the group consisting of an anti-CTLA$_4$ antibody, an anti-PD-1 antibody, an anti-PD-Li antibody, a chimeric antigen receptor T cell, irradiation therapy, chemotherapy and a cancer cell-targeting antibody, and wherein the irAE is selected from the group consisting of a gastrointestinal disorder; pure red cell aplasia; microcytic anemia; lupus; autoimmune nephritis; autoimmune hepatitis; pneumonitis; heart disease; endocrinopathy; Addison's disease; hypogonadism; Sjogren's syndrome; and type I diabetes.

2. The method of claim 1, wherein the anti-CTLA$_4$ antibody is Ipilimumab.

3. The method of claim 1, wherein the anti-CTLA$_4$ antibody is administered in combination with another therapy.

4. The method of claim 1, wherein the anti-PD-1 antibody or anti-PD-Li antibody is administered in combination with another therapy.

5. The method of claim 1, wherein the cancer therapy is selected from the group consisting of irradiation therapy; chemotherapy; and a cancer cell-targeting antibody.

6. The method of claim 1, wherein the CD24 protein further comprises a Fc region of a mammalian immunoglobin (Ig) protein, wherein the Fc region is fused at the N-terminus or C-terminus of the CD24 protein.

7. The method of claim 6, wherein the Ig protein is human.

8. The method of claim 7, wherein the Fc region comprises a hinge region and CH2 and CH3 domains of the human Ig protein, and wherein the Ig is selected from the group consisting of IgG1, IgG2, IgG3, IgG4, and IgA.

9. The method of claim 7, wherein the Fc region comprises a hinge region and CH2, CH3 and CH4 domains of IgM.

10. The method of claim 8, wherein the sequence of the CD24 protein comprises the amino acid sequence set forth in SEQ ID NO: 6, 11, or 12.

11. The method of claim 1, wherein the CD24 protein is produced using a eukaryotic protein expression system.

12. The method of claim 11, wherein the expression system comprises a vector contained in a Chinese Hamster Ovary cell line or a replication-defective retroviral vector.

13. The method of claim 1, wherein the irAE is a heart disease selected from the group consisting of such as myocarditis and pericarditis.

14. The method of claim 1, wherein the CD24 protein is glycosylated.

15. The method of claim 1, wherein the sequence of the CD24 protein consists of the sequence set forth in SEQ ID NO: 6, 11, or 12.

16. A method of treating immune-related adverse events (irAEs) associated with a cancer therapy in a subject in need thereof, comprising administering to the subject a CD24 protein comprising a mature soluble human CD24 comprising an amino acid sequence set forth in SEQ ID NO: 1, wherein the cancer therapy is selected from the group consisting irradiation therapy, chemotherapy and a cancer cell-targeting antibody, and wherein the irAE is selected from the group consisting of a gastrointestinal disorder; heart disease; endocrinopathy and type I diabetes.

* * * * *

SEQUENCE LISTING

```
<160> NUMBER OF SEQ ID NOS: 12

<210> SEQ ID NO 1
<211> LENGTH: 31
<212> TYPE: PRT
<213> ORGANISM: Homo sapiens
<220> FEATURE:
<221> NAME/KEY: VARIANT
<222> LOCATION: (31)...(31)
<223> OTHER INFORMATION: Valine or Alanine
```

-continued

```
<400> SEQUENCE: 1

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Xaa
            20                  25                  30

<210> SEQ ID NO 2
<211> LENGTH: 30
<212> TYPE: PRT
<213> ORGANISM: Homo sapiens

<400> SEQUENCE: 2

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys
            20                  25                  30

<210> SEQ ID NO 3
<211> LENGTH: 27
<212> TYPE: PRT
<213> ORGANISM: Mus musculus

<400> SEQUENCE: 3

Asn Gln Thr Ser Val Ala Pro Phe Pro Gly Asn Gln Asn Ile Ser Ala
1               5                   10                  15

Ser Pro Asn Pro Thr Asn Ala Thr Thr Arg Gly
            20                  25

<210> SEQ ID NO 4
<211> LENGTH: 26
<212> TYPE: PRT
<213> ORGANISM: Homo sapiens

<400> SEQUENCE: 4

Met Gly Arg Ala Met Val Ala Arg Leu Gly Leu Gly Leu Leu Leu Leu
1               5                   10                  15

Ala Leu Leu Leu Pro Thr Gln Ile Tyr Ser
            20                  25

<210> SEQ ID NO 5
<211> LENGTH: 287
<212> TYPE: PRT
<213> ORGANISM: Artificial
<220> FEATURE:
<223> OTHER INFORMATION: Fusion protein

<400> SEQUENCE: 5

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Pro Lys Ser Cys Asp Lys Thr His
    50                  55                  60

Thr Cys Pro Pro Cys Pro Ala Pro Glu Leu Leu Gly Gly Pro Ser Val
65                  70                  75                  80

Phe Leu Phe Pro Pro Lys Pro Lys Asp Thr Leu Met Ile Ser Arg Thr
                85                  90                  95
```

Pro Glu Val Thr Cys Val Val Asp Val Ser His Glu Asp Pro Glu
            100                 105                 110

Val Lys Phe Asn Trp Tyr Val Asp Gly Val Glu Val His Asn Ala Lys
        115                 120                 125

Thr Lys Pro Arg Glu Glu Gln Tyr Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Arg Asp Glu Leu Thr Lys Asn Gln Val Ser Leu Thr Cys Leu
        195                 200                 205

Val Lys Gly Phe Tyr Pro Ser Asp Ile Ala Val Glu Trp Glu Ser Asn
    210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Lys Leu Thr Val Asp Lys Ser Arg
                245                 250                 255

Trp Gln Gln Gly Asn Val Phe Ser Cys Ser Val Met His Glu Ala Leu
            260                 265                 270

His Asn His Tyr Thr Gln Lys Ser Leu Ser Leu Ser Pro Gly Lys
        275                 280                 285

<210> SEQ ID NO 6
<211> LENGTH: 261
<212> TYPE: PRT
<213> ORGANISM: Artificial
<220> FEATURE:
<223> OTHER INFORMATION: Fusion protein

<400> SEQUENCE: 6

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

```
Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
            195                 200                 205

Pro Pro Val Leu Asp Ser Asp Gly Ser Phe Phe Leu Tyr Ser Lys Leu
            210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260

<210> SEQ ID NO 7
<211> LENGTH: 231
<212> TYPE: PRT
<213> ORGANISM: Homo sapiens

<400> SEQUENCE: 7

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 8
<211> LENGTH: 288
<212> TYPE: PRT
<213> ORGANISM: Artificial
<220> FEATURE:
<223> OTHER INFORMATION: Fusion protein
```

<400> SEQUENCE: 8

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
                20                  25                  30

Thr Ser Ser Asn Ser Ser Gln Ser Thr Ser Asn Ser Gly Leu Ala Pro
            35                  40                  45

Asn Pro Thr Asn Ala Thr Thr Lys Val Pro Lys Ser Cys Asp Lys Thr
50                  55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
                100                 105                 110

Glu Val Lys Phe Asn Trp Tyr Val Asp Gly Val Glu Val His Asn Ala
            115                 120                 125

Lys Thr Lys Pro Arg Glu Glu Gln Tyr Asn Ser Thr Tyr Arg Val Val
130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Asp Glu Leu Thr Lys Asn Gln Val Ser Leu Thr Cys
            195                 200                 205

Leu Val Lys Gly Phe Tyr Pro Ser Asp Ile Ala Val Glu Trp Glu Ser
210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
            275                 280                 285
```

<210> SEQ ID NO 9
<211> LENGTH: 288
<212> TYPE: PRT
<213> ORGANISM: Artificial
<220> FEATURE:
<223> OTHER INFORMATION: Fusion protein

<400> SEQUENCE: 9

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
                20                  25                  30

Thr Ser Ser Asn Ser Ser Gln Ser Thr Ser Asn Ser Gly Leu Ala Pro
            35                  40                  45

Asn Pro Thr Asn Ala Thr Thr Lys Ala Pro Lys Ser Cys Asp Lys Thr
50                  55                  60
```

```
His Thr Cys Pro Pro Cys Pro Ala Pro Glu Leu Leu Gly Gly Pro Ser
 65                  70                  75                  80

Val Phe Leu Phe Pro Pro Lys Pro Lys Asp Thr Leu Met Ile Ser Arg
                 85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
        115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Asp Glu Leu Thr Lys Asn Gln Val Ser Leu Thr Cys
        195                 200                 205

Leu Val Lys Gly Phe Tyr Pro Ser Asp Ile Ala Val Glu Trp Glu Ser
210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
        275                 280                 285

<210> SEQ ID NO 10
<211> LENGTH: 29
<212> TYPE: PRT
<213> ORGANISM: Macaca fascicularis

<400> SEQUENCE: 10

Thr Val Thr Thr Ser Ala Pro Leu Ser Ser Asn Ser Pro Gln Asn Thr
  1               5                  10                  15

Ser Thr Thr Pro Asn Pro Ala Asn Thr Thr Lys Ala
                 20                  25

<210> SEQ ID NO 11
<211> LENGTH: 262
<212> TYPE: PRT
<213> ORGANISM: Artificial
<220> FEATURE:
<223> OTHER INFORMATION: Fusion protein

<400> SEQUENCE: 11

Ser Glu Thr Thr Thr Gly Thr Ser Ser Asn Ser Ser Gln Ser Thr Ser
  1               5                  10                  15

Asn Ser Gly Leu Ala Pro Asn Pro Thr Asn Ala Thr Thr Lys Val Pro
                 20                  25                  30

Lys Ser Cys Asp Lys Thr His Thr Cys Pro Pro Cys Pro Ala Pro Glu
            35                  40                  45

Leu Leu Gly Gly Pro Ser Val Phe Leu Phe Pro Pro Lys Pro Lys Asp
 50                  55                  60
```

```
Thr Leu Met Ile Ser Arg Thr Pro Glu Val Thr Cys Val Val Val Asp
 65                  70                  75                  80

Val Ser His Glu Asp Pro Glu Val Lys Phe Asn Trp Tyr Val Asp Gly
                 85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Lys
            260

<210> SEQ ID NO 12
<211> LENGTH: 262
<212> TYPE: PRT
<213> ORGANISM: Artificial
<220> FEATURE:
<223> OTHER INFORMATION: Fusion protein

<400> SEQUENCE: 12

Ser Glu Thr Thr Thr Gly Thr Ser Ser Asn Ser Ser Gln Ser Thr Ser
 1               5                  10                  15

Asn Ser Gly Leu Ala Pro Asn Pro Thr Asn Ala Thr Thr Lys Ala Pro
             20                  25                  30

Lys Ser Cys Asp Lys Thr His Thr Cys Pro Pro Cys Pro Ala Pro Glu
         35                  40                  45

Leu Leu Gly Gly Pro Ser Val Phe Leu Phe Pro Pro Lys Pro Lys Asp
     50                  55                  60

Thr Leu Met Ile Ser Arg Thr Pro Glu Val Thr Cys Val Val Val Asp
 65                  70                  75                  80

Val Ser His Glu Asp Pro Glu Val Lys Phe Asn Trp Tyr Val Asp Gly
                 85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160
```

```
Pro Gln Val Tyr Thr Leu Pro Pro Ser Arg Asp Glu Leu Thr Lys Asn
                165                 170                 175
Gln Val Ser Leu Thr Cys Leu Val Lys Gly Phe Tyr Pro Ser Asp Ile
            180                 185                 190
Ala Val Glu Trp Glu Ser Asn Gly Gln Pro Glu Asn Asn Tyr Lys Thr
        195                 200                 205
Thr Pro Pro Val Leu Asp Ser Asp Gly Ser Phe Phe Leu Tyr Ser Lys
    210                 215                 220
Leu Thr Val Asp Lys Ser Arg Trp Gln Gln Gly Asn Val Phe Ser Cys
225                 230                 235                 240
Ser Val Met His Glu Ala Leu His Asn His Tyr Thr Gln Lys Ser Leu
                245                 250                 255
Ser Leu Ser Pro Gly Lys
            260
```